US005747241A

United States Patent [19]
Miyamura et al.

[11] Patent Number: 5,747,241
[45] Date of Patent: May 5, 1998

[54] DIAGNOSTIC REAGENT FOR HEPATITIS C

[75] Inventors: Tatsuo Miyamura; Izumu Saito; Shizuko Harada, all of Tokyo-to; Yoshikazu Honda, Kamakura, all of Japan

[73] Assignee: Japan as represented by Director General of Agency of National Institute of Health, Tokyo, Japan

[21] Appl. No.: 460,806

[22] Filed: Jun. 2, 1995

Related U.S. Application Data

[62] Division of Ser. No. 325,630, Oct. 19, 1994, which is a continuation of Ser. No. 956,993, Oct. 6, 1992, abandoned.

[30] Foreign Application Priority Data

Oct. 8, 1991 [JP] Japan ................................. 3-260824

[51] Int. Cl.⁶ .................. G01N 33/576; C12P 21/02; C07K 14/18
[52] U.S. Cl. ............... 435/5; 530/350; 436/518; 436/820; 435/69.3
[58] Field of Search .................... 435/5, 7.1, 69.3; 436/513, 518, 536, 543, 820; 530/350

[56] References Cited

U.S. PATENT DOCUMENTS

| | | | |
|---|---|---|---|
| 5,106,726 | 4/1992 | Wang | 435/5 |
| 5,350,671 | 9/1994 | Houghton et al. | 435/5 |

FOREIGN PATENT DOCUMENTS

| | | |
|---|---|---|
| 0 388 232 | 9/1990 | European Pat. Off. . |
| 0 463 848 | 1/1992 | European Pat. Off. . |
| 0 472 207 | 2/1992 | European Pat. Off. . |
| 0 518 313 | 12/1992 | European Pat. Off. . |
| WO 92/08734 | 5/1992 | WIPO . |

OTHER PUBLICATIONS

Japan J. Exp. Med., vol. 60, No. 3, pp. 167–177, 1990, Hiroaki Okamoto, et al., "The 5′–Terminal Sequence of the Hepatitis C Virus Genome".
Viral Hepatitis and Liver Disease, Jun. 1, 1991, George Kuo, et al., "Serodiagnosis of Hepatitis C Viral Infection Using Recombinant–Based Assays for Circulating Antibodies to Different Viral Proteins", pp. 347–349.
Virology, vol. 180, pp. 842–848, 1991, Amy J. Weiner, et al., "Variable and Hypervariable Domains are Found in the Regions HCV Corresponding to the Flavivirus Envelope and NS1 Proteins and the Pestivirus Envelope Glycoproteins".
Hepatology, vol. 16, No. 4, p. 226A, 1992, Osamu Yokosuka, et al., "Detection of Anti–Hepatitis C Virus E2/NS1 Antibody in Patients With Type C Liver Disease by Western Blotting".
Biochemical and Biophysical Research Communications, vol. 172, No. 2, Oct. 30, 1990, pp. 511–516, Kanae Muraiso, et al., "A Structural Protein of Hepatitis C Virus Expressed in E. coli Facilitates Accurate Detection of Hepatitis C Virus".

Proc. Natl. Acad. Sci. USA, vol. 88, pp. 4641–4645, Jun. 1991, Joe Chiba, et al., "Serodiagnosis of Hepatitis C Virus (HCV) Infection with an HCV Core Protein Molecularly Expressed by a Recombinant Baculovirus".
The Lancet, vol. 337, Feb. 9, 1991, pp. 317–319, C. L. Van Der Poel, et al., "Confirmation of Hepatitis C Virus Infection by New Four–Antigen Recombinant Immunoblot Assay".
Journal of Clinical Microbiology, vol. 29, No. 11, Nov. 1991, pp. 2616–2617, R. K. Chaudhary, et al., "Evaluation of Hepatitis C Virus Kits".
Hepatology, vol. 15, No. 3, 1992, pp. 391–394, Tohru Katayama, et al., "Improved Serodiagnosis of Non–A, Non–B Hepatitis by an Assay Detecting Antibody to Hepatitis C Virus Core Antigen".
Hepatology, vol. 15, No. 2, 1992, pp. 350–353, Harvey J. Alter, et al., "New Kit on the Block: Evaluation of Second-–Generation Assays for Detection of Antibody to the Hepatitis C Virus".
Hepatology, vol. 15, No. 2, 1992, pp. 187–190, Lennox J. Jeffers, et al., "Prevalence of Antibodies to Hepatitis C Virus Among Patients with Cryptogenic Chronic Hepatitis and Cirrhosis".
Hepatology, vol. 15, No. 2, 1992, pp. 180–186, Hiroaki Okamoto, et al., "Antibodies Against Synthetic Oligopeptides Deduced From the Putative Core Gene for the Diagnosis of Hepatitis C Virus Infection".
Hepatology, vol. 15, No. 2, 1992, pp. 175–179, Jonathan Brown, et al., "Seroprevalence of Hepatitis C Virus Nucleocapsid Antibodies in Patients With Cryptogenic Chronic Liver Disease".
Hepatology, vol. 15, No. 1, 1992, pp. 19–25, John G. McHutchison, et al., "Improved Detection of Hepatitis C Virus Antibodies in High–Risk Populations".
Proc. Natl. Acad. Sci. USA, vol. 89, pp. 4486–4489, May 1992, Girish J. Kotwal, et al., "Detection of Acute Hepatitis C Virus Infection by Elisa Using a Synthetic Peptide Comprising a Structural Epitope".
Proc. Natl. Acad. Sci. USA, vol. 89, pp. 3190–3194, Apr. 1992, Wei–Mei Ching, et al., "Interaction of Immune Sera With Synthetic Peptides Corresponding to the Structural Protein Region of Hepatitis C Virus".

(List continued on next page.)

Primary Examiner—Marian C. Knode
Assistant Examiner—Donna C. Wortman
Attorney, Agent, or Firm—Oblon, Spivak, McClelland, Maier & Neustadt, P.C.

[57] ABSTRACT

A diagnostic reagent for hepatitis C, which detects an antibody induced by infection of hepatitis C virus, comprising the second envelope protein or first non-structural protein which is encoded by the gene of hepatitis C virus and has a sugar chain. This invention also provides a method for detecting an anti-hepatitis C virus antibody. The use of the diagnostic reagent for hepatitis C according to the present invention makes highly sensitive diagnosis of hepatitis C possible.

6 Claims, 6 Drawing Sheets

OTHER PUBLICATIONS

Journal of Clinical Microbiology, vol. 30, No. 3, Mar. 1992, pp. 552–556, David S. Vallari, et al., "Serological Markers of Posttransfusion Hepatitis C Viral Infection".

Journal of Virology, vol. 66, No. 3, Mar. 1992, pp. 1425–1431, Yoshiharu Matsuura, et al., "Expression of Processed Envelope Protein of Hepatitis C Virus in Mammalian and Insect Cells".

Biochemical and Biophysical Research Communications, vol. 183, No. 3, Mar. 31, 1992, pp. 925–930, Eiji Mita, et al., "Expression of MBP–HCV NS1/E2 Fusion in *E. coli* and Detection of Anti–NS1/E2 Antibody in Type C Chronic Liver Disease".

Hepatology, vol. 14, No. 5, 1991, pp. 756–762, Anna S.F. Lok, et al.,"Overestimation of the Prevalence of Antibody to Hepatitis C Virus in Retrospective Studies on Stored Sera".

Hepatology, vol. 14, No. 2, 1991, pp. 381–388, Michael Houghton, et al., "Molecular Biology of the Hepatitis C Viruses: Implications for Diagnosis, Development and Control of Viral Disease".

Hepatology, vol. 14, No. 1, 1991, pp. 38–43, Juan Antonio Quiroga, et al., "IGM Antibody to Hepatitis C Virus in Acute and Chronic Hepatitis C".

Science, vol. 244, Apr. 21, 1989, pp. 362–364, G. Kuo, et al. "An Assay for Circulating AntiBodies to a Major Etiologic Virus of Human Non–A, Non–B Hepatitis".

Proc. Natl. Acad. Sci. USA, vol. 88, pp. 2451–2455, Mar. 1991, Q. L. Choo, et al., "Genetic Organization and Diversity of the Hepatitis C Virus".

Hijikata et al., Hypervariable Regions in the Putative Glycoprotein of Hepatitis C Virus, Biochem. Biophys. Res. Commun. 175, 220–228, 1991.

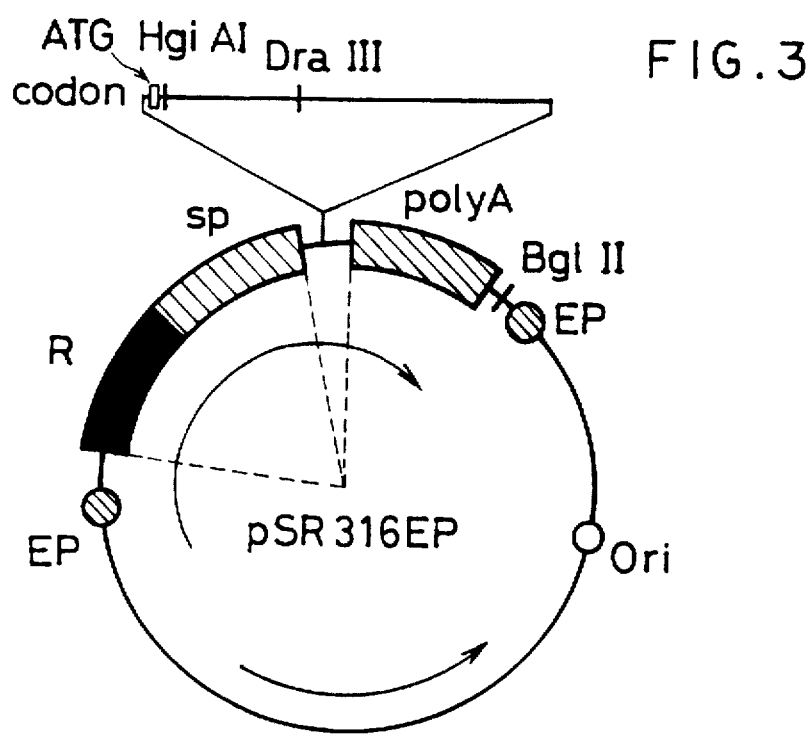
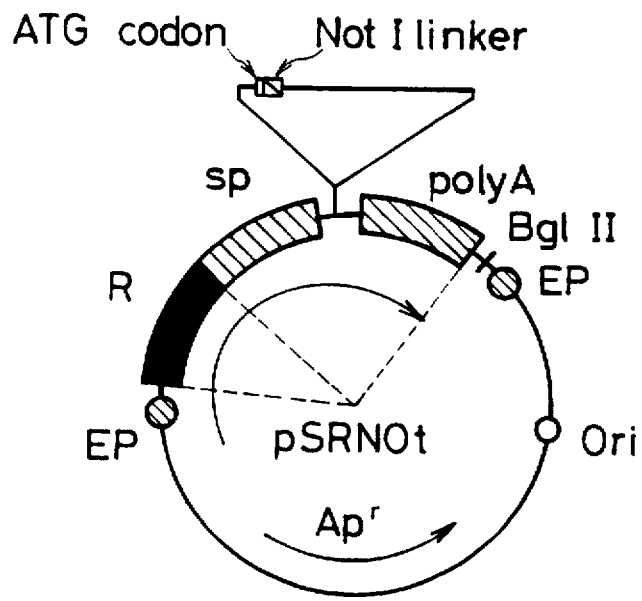
FIG. 3

FIG. 4
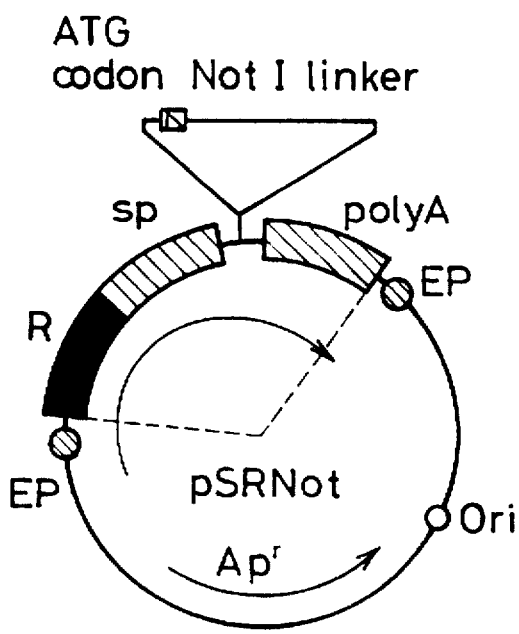
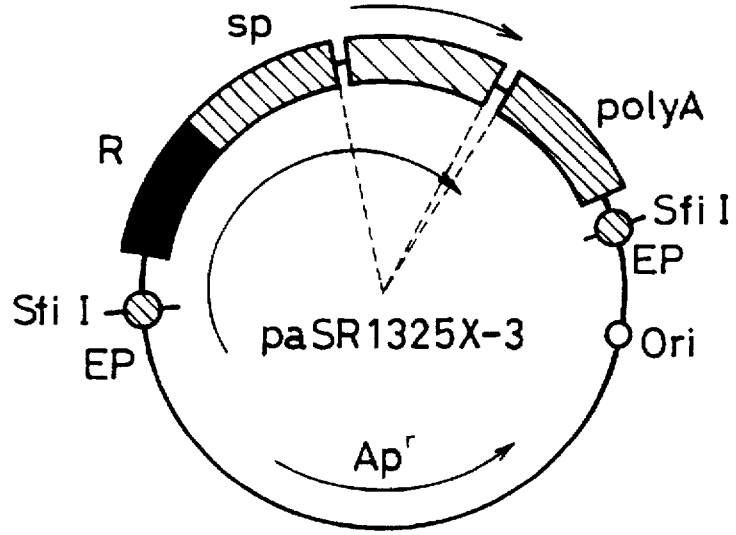

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Hepatitis C virus ( v i i ) IMMEDIATE SOURCE:
        ( B ) CLONE: J1-1325

( i x ) FEATURE:
        ( A ) NAME/KEY: CDS
        ( B ) LOCATION: 2..1207

( x i ) SEQUENCE DESCRIPTION: SEQ ID NO:1:

```
G ATC CCA CAA GCT GTC ATG GAC ATG GTG GCG GGG GCC CAC TGG GGA          46
  Ile Pro Gln Ala Val Met Asp Met Val Ala Gly Ala His Trp Gly
  1               5                  10                 15

GTC CTA GCG GGC CTT GCC TAC TAT TCC ATG GTG GGG AAC TGG GCT AAG        94
Val Leu Ala Gly Leu Ala Tyr Tyr Ser Met Val Gly Asn Trp Ala Lys
               20                  25                  30

GTT TTG ATT GTG ATG CTA CTC TTT GCC GGC GTT GAC GGG CAT ACC CGC       142
Val Leu Ile Val Met Leu Leu Phe Ala Gly Val Asp Gly His Thr Arg
                35                 40                  45

GTG ACG GGG GGG GTG CAA GGC CAT GTC ACC TCT ACA CTC ACG TCC CTC       190
Val Thr Gly Gly Val Gln Gly His Val Thr Ser Thr Leu Thr Ser Leu
            50                  55                  60
```

| | | | | | | | | | | | | | | | | |
|---|---|---|---|---|---|---|---|---|---|---|---|---|---|---|---|---|
| TTT | AGA | CCT | GGG | GCG | TCC | CAG | AAA | ATT | CAG | CTT | GTA | AAC | ACC | AAT | GGC | 238 |
| Phe | Arg | Pro | Gly | Ala | Ser | Gln | Lys | Ile | Gln | Leu | Val | Asn | Thr | Asn | Gly | |
| | 65 | | | | | 70 | | | | | 75 | | | | | |
| AGT | TGG | CAT | ATC | AAC | AGG | ACT | GCC | CTG | AAC | TGC | AAT | GAC | TCC | CTC | AAA | 286 |
| Ser | Trp | His | Ile | Asn | Arg | Thr | Ala | Leu | Asn | Cys | Asn | Asp | Ser | Leu | Lys | |
| 80 | | | | | 85 | | | | | 90 | | | | | 95 | |
| ACT | GGG | TTT | CTT | GCC | GCG | CTG | TTC | TAC | ACA | CAC | AAG | TTC | AAC | GCG | TCC | 334 |
| Thr | Gly | Phe | Leu | Ala | Ala | Leu | Phe | Tyr | Thr | His | Lys | Phe | Asn | Ala | Ser | |
| | | | | 100 | | | | | 105 | | | | | 110 | | |
| GGA | TGC | CCG | GAG | CGC | ATG | GCC | AGC | TGT | CGC | TCC | ATT | GAC | AAG | TTC | GAC | 382 |
| Gly | Cys | Pro | Glu | Arg | Met | Ala | Ser | Cys | Arg | Ser | Ile | Asp | Lys | Phe | Asp | |
| | | | 115 | | | | | 120 | | | | | 125 | | | |
| CAG | GGA | TGG | GGT | CCC | ATC | ACC | TAT | GCT | CAA | CCT | GAC | AAC | TCG | GAC | CAG | 430 |
| Gln | Gly | Trp | Gly | Pro | Ile | Thr | Tyr | Ala | Gln | Pro | Asp | Asn | Ser | Asp | Gln | |
| | | 130 | | | | | 135 | | | | | 140 | | | | |
| AGG | CCG | TAT | TGC | TGG | CAC | TAC | GCA | CCT | CGA | CAG | TGT | GGT | ATC | GTA | CCC | 478 |
| Arg | Pro | Tyr | Cys | Trp | His | Tyr | Ala | Pro | Arg | Gln | Cys | Gly | Ile | Val | Pro | |
| | 145 | | | | | 150 | | | | | 155 | | | | | |
| GCG | TCG | CAG | GTG | TGC | GGT | CCA | GTG | TAT | TGC | TTC | ACC | CCA | AGC | CCT | GTT | 526 |
| Ala | Ser | Gln | Val | Cys | Gly | Pro | Val | Tyr | Cys | Phe | Thr | Pro | Ser | Pro | Val | |
| 160 | | | | | 165 | | | | | 170 | | | | | 175 | |
| GTA | GTG | GGG | ACG | ACC | GAT | CGT | TTC | GGC | GCC | CCT | ACG | TAT | AAC | TGG | GGG | 574 |
| Val | Val | Gly | Thr | Thr | Asp | Arg | Phe | Gly | Ala | Pro | Thr | Tyr | Asn | Trp | Gly | |
| | | | | 180 | | | | | 185 | | | | | 190 | | |
| GAC | AAT | GAG | ACG | GAC | GTG | CTG | CTC | CTA | AAC | AAC | ACG | CGG | CCG | CCG | CAT | 622 |
| Asp | Asn | Glu | Thr | Asp | Val | Leu | Leu | Leu | Asn | Asn | Thr | Arg | Pro | Pro | His | |
| | | | 195 | | | | | 200 | | | | | 205 | | | |
| GGC | AAC | TGG | TTC | GGC | TGT | ACA | TGG | ATG | AAT | AGC | ACT | GGG | TTC | ACC | AAG | 670 |
| Gly | Asn | Trp | Phe | Gly | Cys | Thr | Trp | Met | Asn | Ser | Thr | Gly | Phe | Thr | Lys | |
| | | 210 | | | | | 215 | | | | | 220 | | | | |
| ACG | TGC | GGA | GGC | CCC | CCG | TGT | AAC | ATC | AGG | GGG | GTC | GGC | AAC | AAC | ACC | 718 |
| Thr | Cys | Gly | Gly | Pro | Pro | Cys | Asn | Ile | Arg | Gly | Val | Gly | Asn | Asn | Thr | |
| | 225 | | | | | 230 | | | | | 235 | | | | | |
| TTG | ACC | TGC | CCC | ACG | GAC | TGC | TTC | CGG | AAG | CAC | CCC | GAC | GCC | ACT | TAC | 766 |
| Leu | Thr | Cys | Pro | Thr | Asp | Cys | Phe | Arg | Lys | His | Pro | Asp | Ala | Thr | Tyr | |
| 240 | | | | | 245 | | | | | 250 | | | | | 255 | |
| ACA | AAA | TGT | GGT | TCG | GGC | CCT | TGG | TTG | ACA | CCT | AGG | TGC | TTG | GTT | GAC | 814 |
| Thr | Lys | Cys | Gly | Ser | Gly | Pro | Trp | Leu | Thr | Pro | Arg | Cys | Leu | Val | Asp | |
| | | | | 260 | | | | | 265 | | | | | 270 | | |
| TAC | CCA | TAC | AGG | CTC | TGG | CAC | TAC | CCC | TGC | ACT | GTC | AAC | TTT | ACC | ATC | 862 |
| Tyr | Pro | Tyr | Arg | Leu | Trp | His | Tyr | Pro | Cys | Thr | Val | Asn | Phe | Thr | Ile | |
| | | | 275 | | | | | 280 | | | | | 285 | | | |
| TTC | AAG | GTT | AGG | ATG | TAT | GTG | GGG | GGC | GTG | GAG | CAC | AGG | CTT | GAT | GCT | 910 |
| Phe | Lys | Val | Arg | Met | Tyr | Val | Gly | Gly | Val | Glu | His | Arg | Leu | Asp | Ala | |
| | | 290 | | | | | 295 | | | | | 300 | | | | |
| GCA | TGC | AAC | TGG | ACT | CGA | GGA | GAG | CGT | TGC | GAC | TTG | GAG | GAC | AGG | GAT | 958 |
| Ala | Cys | Asn | Trp | Thr | Arg | Gly | Glu | Arg | Cys | Asp | Leu | Glu | Asp | Arg | Asp | |
| | 305 | | | | | 310 | | | | | 315 | | | | | |
| AGA | GCA | GAG | CTC | AGC | CCG | CTA | CTG | CTG | TCT | ACG | ACA | GAG | TGG | CAG | GTA | 1006 |
| Arg | Ala | Glu | Leu | Ser | Pro | Leu | Leu | Leu | Ser | Thr | Thr | Glu | Trp | Gln | Val | |
| 320 | | | | | 325 | | | | | 330 | | | | | 335 | |
| CTG | CCC | TGT | TCC | TTC | ACC | ACC | CTA | CCG | GCT | CTG | TCC | ACT | GGT | CTA | ATC | 1054 |
| Leu | Pro | Cys | Ser | Phe | Thr | Thr | Leu | Pro | Ala | Leu | Ser | Thr | Gly | Leu | Ile | |
| | | | | 340 | | | | | 345 | | | | | 350 | | |
| CAT | CTC | CAT | CAG | AAC | GTC | GTG | GAC | GTG | CAA | TAC | CTG | TAC | GGT | ATA | GGG | 1102 |
| His | Leu | His | Gln | Asn | Val | Val | Asp | Val | Gln | Tyr | Leu | Tyr | Gly | Ile | Gly | |
| | | | 355 | | | | | 360 | | | | | 365 | | | |
| TCA | GCA | GTT | GTC | TCC | TTT | GTA | ATC | AAA | TGG | GAG | TAT | GTC | CTG | TTG | CTT | 1150 |
| Ser | Ala | Val | Val | Ser | Phe | Val | Ile | Lys | Trp | Glu | Tyr | Val | Leu | Leu | Leu | |
| | | 370 | | | | | 375 | | | | | 380 | | | | |

```
TTC CTT CTC CTG GCT GAC GCA CGC GTC TGT GCC TGC TTG TGG ATG ATG      1198
Phe Leu Leu Leu Ala Asp Ala Arg Val Cys Ala Cys Leu Trp Met Met
    385                 390                 395

CTG CTG ATA                                                           1207
Leu Leu Ile
400
```

( 2 ) INFORMATION FOR SEQ ID NO:2:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ile Pro Gln Ala Val Met Asp Met Val Ala Gly Ala His Trp Gly Val
1               5                   10                  15

Leu Ala Gly Leu Ala Tyr Tyr Ser Met Val Gly Asn Trp Ala Lys Val
            20                  25                  30

Leu Ile Val Met Leu Leu Phe Ala Gly Val Asp Gly His Thr Arg Val
        35                  40                  45

Thr Gly Gly Val Gln Gly His Val Thr Ser Thr Leu Thr Ser Leu Phe
    50                  55                  60

Arg Pro Gly Ala Ser Gln Lys Ile Gln Leu Val Asn Thr Asn Gly Ser
65                  70                  75                  80

Trp His Ile Asn Arg Thr Ala Leu Asn Cys Asn Asp Ser Leu Lys Thr
                85                  90                  95

Gly Phe Leu Ala Ala Leu Phe Tyr Thr His Lys Phe Asn Ala Ser Gly
                100                 105                 110

Cys Pro Glu Arg Met Ala Ser Cys Arg Ser Ile Asp Lys Phe Asp Gln
            115                 120                 125

Gly Trp Gly Pro Ile Thr Tyr Ala Gln Pro Asp Asn Ser Asp Gln Arg
    130                 135                 140

Pro Tyr Cys Trp His Tyr Ala Pro Arg Gln Cys Gly Ile Val Pro Ala
145                 150                 155                 160

Ser Gln Val Cys Gly Pro Val Tyr Cys Phe Thr Pro Ser Pro Val Val
                165                 170                 175

Val Gly Thr Thr Asp Arg Phe Gly Ala Pro Thr Tyr Asn Trp Gly Asp
                180                 185                 190

Asn Glu Thr Asp Val Leu Leu Leu Asn Asn Thr Arg Pro Pro His Gly
            195                 200                 205

Asn Trp Phe Gly Cys Thr Trp Met Asn Ser Thr Gly Phe Thr Lys Thr
    210                 215                 220

Cys Gly Gly Pro Pro Cys Asn Ile Arg Gly Val Gly Asn Asn Thr Leu
225                 230                 235                 240

Thr Cys Pro Thr Asp Cys Phe Arg Lys His Pro Asp Ala Thr Tyr Thr
                245                 250                 255

Lys Cys Gly Ser Gly Pro Trp Leu Thr Pro Arg Cys Leu Val Asp Tyr
            260                 265                 270

Pro Tyr Arg Leu Trp His Tyr Pro Cys Thr Val Asn Phe Thr Ile Phe
    275                 280                 285

Lys Val Arg Met Tyr Val Gly Gly Val Glu His Arg Leu Asp Ala Ala
290                 295                 300

Cys Asn Trp Thr Arg Gly Glu Arg Cys Asp Leu Glu Asp Arg Asp Arg
305                 310                 315                 320
```

```
Ala Glu Leu Ser Pro Leu Leu Leu Ser Thr Thr Glu Trp Gln Val Leu
            325             330             335

Pro Cys Ser Phe Thr Thr Leu Pro Ala Leu Ser Thr Gly Leu Ile His
            340             345             350

Leu His Gln Asn Val Val Asp Val Gln Tyr Leu Tyr Gly Ile Gly Ser
            355             360             365

Ala Val Val Ser Phe Val Ile Lys Trp Glu Tyr Val Leu Leu Leu Phe
    370             375             380

Leu Leu Leu Ala Asp Ala Arg Val Cys Ala Cys Leu Trp Met Met Leu
385             390             395             400

Leu Ile
```

(2) INFORMATION FOR SEQ ID NO:3:

(i) SEQUENCE CHARACTERISTICS:
        (A) LENGTH: 1207 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
        (A) ORGANISM: Hepatitis C virus (vii) IMMEDIATE SOURCE:
        (B) CLONE: N27MX24A-2

(ix) FEATURE:
        (A) NAME/KEY: CDS
        (B) LOCATION: 2..1207

(xi) SEQUENCE DESCRIPTION: SEQ ID NO:3:

```
G ATC CCA CAA GCC GTG GTG GAT ATG GTG GCA GGG GCC CAC TGG GGA        46
  Ile Pro Gln Ala Val Val Asp Met Val Ala Gly Ala His Trp Gly
   1               5                  10                  15

GTC CTG GCG GGC CTT GCC TAC TAT TCC ATG GTG GGG AAC TGG GCT AAG      94
Val Leu Ala Gly Leu Ala Tyr Tyr Ser Met Val Gly Asn Trp Ala Lys
                    20                  25                  30

GTC TTG GTT GTG ATG CTG CTC TTC GCC GGT GTT GAC GGG GGG ACC CAC     142
Val Leu Val Val Met Leu Leu Phe Ala Gly Val Asp Gly Gly Thr His
                35                  40                  45

GTG ACA GGG GGG AAG GTA GCC TAC ACC ACC CAG GGC TTT ACA CCC TTC     190
Val Thr Gly Gly Lys Val Ala Tyr Thr Thr Gln Gly Phe Thr Pro Phe
        50                  55                  60

TTT TCA CGA GGG CCG TCT CAG AAA ATC CAA CTT GTA AAC ACT AAC GGC     238
Phe Ser Arg Gly Pro Ser Gln Lys Ile Gln Leu Val Asn Thr Asn Gly
    65                  70                  75

AGC TGG CAC ATC AAT AGG ACT GCC CTC AAT TGC AAT GAC TCC CTT AAC     286
Ser Trp His Ile Asn Arg Thr Ala Leu Asn Cys Asn Asp Ser Leu Asn
80                  85                  90                  95

ACC GGG TTC CTT GCC GCG CTG TTC TAC ACC CAC AGC TTC AAC GCG TCC     334
Thr Gly Phe Leu Ala Ala Leu Phe Tyr Thr His Ser Phe Asn Ala Ser
                100                 105                 110

GGA TGT CCG GAG CGT ATG GCC GGT TGC CGC CCC ATT GAC GAG TTC GCT     382
Gly Cys Pro Glu Arg Met Ala Gly Cys Arg Pro Ile Asp Glu Phe Ala
                115                 120                 125

CAG GGG TGG GGT CCC ATC ACT CAT GTT GTG CCT AAC ATC TCG GAC CAG     430
Gln Gly Trp Gly Pro Ile Thr His Val Val Pro Asn Ile Ser Asp Gln
            130                 135                 140

AGG CCC TAT TGC TGG CAC TAC GCG CCT CGA CCG TGT GGT ATC GTA CCC     478
Arg Pro Tyr Cys Trp His Tyr Ala Pro Arg Pro Cys Gly Ile Val Pro
```

-continued

```
            145                         150                              155
GCG  TCG  CAG  GTG  TGT  GGT  CCG  GTG  TAT  TGC  TTC  ACC  CCA  AGC  CCT  GTT        526
Ala  Ser  Gln  Val  Cys  Gly  Pro  Val  Tyr  Cys  Phe  Thr  Pro  Ser  Pro  Val
160                      165                      170                      175

GTG  GTG  GGG  ACG  ACC  GAT  CGT  TTC  GGC  GCC  CCC  ACG  TAC  AAC  TGG  GGA        574
Val  Val  Gly  Thr  Thr  Asp  Arg  Phe  Gly  Ala  Pro  Thr  Tyr  Asn  Trp  Gly
                    180                      185                      190

AAC  AAT  GAG  ACG  GAT  GTG  CTA  CTC  CTC  AAC  AAC  ACA  CGG  CCG  CCG  CAG        622
Asn  Asn  Glu  Thr  Asp  Val  Leu  Leu  Leu  Asn  Asn  Thr  Arg  Pro  Pro  Gln
               195                      200                      205

GGC  AAC  TGG  TTC  GGT  TGT  ACC  TGG  ATG  AAT  GGC  ACT  GGG  TTC  ACA  AAG        670
Gly  Asn  Trp  Phe  Gly  Cys  Thr  Trp  Met  Asn  Gly  Thr  Gly  Phe  Thr  Lys
          210                      215                      220

ACG  TGC  GGG  GGC  CCC  CCG  TGC  AAC  ATC  GGG  GGG  GTC  GGC  AAC  AAT  ACC        718
Thr  Cys  Gly  Gly  Pro  Pro  Cys  Asn  Ile  Gly  Gly  Val  Gly  Asn  Asn  Thr
     225                      230                      235

TTG  ACT  TGC  CCC  ACG  GAC  TGC  TTC  CGG  AAG  CAC  CCC  GAG  GCC  ACT  TAC        766
Leu  Thr  Cys  Pro  Thr  Asp  Cys  Phe  Arg  Lys  His  Pro  Glu  Ala  Thr  Tyr
240                      245                      250                      255

ACA  AAA  TGT  GGT  TCG  GGG  CCT  TGG  TTG  ACG  CCT  AGG  TGC  CTA  GTT  CAT        814
Thr  Lys  Cys  Gly  Ser  Gly  Pro  Trp  Leu  Thr  Pro  Arg  Cys  Leu  Val  His
                    260                      265                      270

TAC  CCA  TAC  AGG  CTC  TGG  CAC  TAT  CCC  TGC  ACT  GTC  AAC  TTT  ACC  ATC        862
Tyr  Pro  Tyr  Arg  Leu  Trp  His  Tyr  Pro  Cys  Thr  Val  Asn  Phe  Thr  Ile
               275                      280                      285

TTC  AAG  GTT  AGG  ATG  TAT  GTG  GGG  GGC  GTG  GAA  CAC  AGG  CTT  GAA  GCT        910
Phe  Lys  Val  Arg  Met  Tyr  Val  Gly  Gly  Val  Glu  His  Arg  Leu  Glu  Ala
          290                      295                      300

GCA  TGC  AAT  TGG  ACC  CGA  GGA  GAG  CGT  TGT  GAC  TTG  GAG  GAC  AGG  GAT        958
Ala  Cys  Asn  Trp  Thr  Arg  Gly  Glu  Arg  Cys  Asp  Leu  Glu  Asp  Arg  Asp
     305                      310                      315

AGA  TCA  GAG  CTT  AGC  CCG  CTA  TTG  CTG  TCC  ACA  ACA  GAG  TGG  CAG  GTA        1006
Arg  Ser  Glu  Leu  Ser  Pro  Leu  Leu  Leu  Ser  Thr  Thr  Glu  Trp  Gln  Val
320                      325                      330                      335

CTG  CCC  TGT  TCC  TTC  ACC  ACC  CTG  CCG  GCT  CTG  TCC  ACT  GGT  TTG  ATT        1054
Leu  Pro  Cys  Ser  Phe  Thr  Thr  Leu  Pro  Ala  Leu  Ser  Thr  Gly  Leu  Ile
                    340                      345                      350

CAT  CTC  CAT  CAG  AAC  ATC  GTG  GAC  GTG  CAA  TAT  CTG  TAC  GGC  ATA  GGG        1102
His  Leu  His  Gln  Asn  Ile  Val  Asp  Val  Gln  Tyr  Leu  Tyr  Gly  Ile  Gly
               355                      360                      365

TCG  GCG  GTT  GTC  TCC  TTC  GCA  ATC  AAA  TGG  GAA  TAT  ATT  CTG  TTG  CTT        1150
Ser  Ala  Val  Val  Ser  Phe  Ala  Ile  Lys  Trp  Glu  Tyr  Ile  Leu  Leu  Leu
          370                      375                      380

TTC  CTC  CTC  CTG  GCG  GAC  GCG  CGC  GTC  TGT  GCC  TGC  TTG  TGG  ATG  ATG        1198
Phe  Leu  Leu  Leu  Ala  Asp  Ala  Arg  Val  Cys  Ala  Cys  Leu  Trp  Met  Met
385                      390                      395

CTG  CTG  ATA                                                                         1207
Leu  Leu  Ile
400
```

( 2 ) INFORMATION FOR SEQ ID NO:4:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ile  Pro  Gln  Ala  Val  Val  Asp  Met  Val  Ala  Gly  Ala  His  Trp  Gly  Val
  1            5                      10                         15
```

```
Leu Ala Gly Leu Ala Tyr Tyr Ser Met Val Gly Asn Trp Ala Lys Val
            20                  25                  30
Leu Val Val Met Leu Leu Phe Ala Gly Val Asp Gly Gly Thr His Val
        35                  40                  45
Thr Gly Gly Lys Val Ala Tyr Thr Thr Gln Gly Phe Thr Pro Phe Phe
    50                  55                  60
Ser Arg Gly Pro Ser Gln Lys Ile Gln Leu Val Asn Thr Asn Gly Ser
65                      70                  75                  80
Trp His Ile Asn Arg Thr Ala Leu Asn Cys Asn Asp Ser Leu Asn Thr
                85                  90                  95
Gly Phe Leu Ala Ala Leu Phe Tyr Thr His Ser Phe Asn Ala Ser Gly
                100                 105                 110
Cys Pro Glu Arg Met Ala Gly Cys Arg Pro Ile Asp Glu Phe Ala Gln
            115                 120                 125
Gly Trp Gly Pro Ile Thr His Val Val Pro Asn Ile Ser Asp Gln Arg
    130                 135                 140
Pro Tyr Cys Trp His Tyr Ala Pro Arg Pro Cys Gly Ile Val Pro Ala
145                 150                 155                 160
Ser Gln Val Cys Gly Pro Val Tyr Cys Phe Thr Pro Ser Pro Val Val
                165                 170                 175
Val Gly Thr Thr Asp Arg Phe Gly Ala Pro Thr Tyr Asn Trp Gly Asn
            180                 185                 190
Asn Glu Thr Asp Val Leu Leu Leu Asn Asn Thr Arg Pro Pro Gln Gly
        195                 200                 205
Asn Trp Phe Gly Cys Thr Trp Met Asn Gly Thr Gly Phe Thr Lys Thr
    210                 215                 220
Cys Gly Gly Pro Pro Cys Asn Ile Gly Gly Val Gly Asn Asn Thr Leu
225                 230                 235                 240
Thr Cys Pro Thr Asp Cys Phe Arg Lys His Pro Glu Ala Thr Tyr Thr
                245                 250                 255
Lys Cys Gly Ser Gly Pro Trp Leu Thr Pro Arg Cys Leu Val His Tyr
            260                 265                 270
Pro Tyr Arg Leu Trp His Tyr Pro Cys Thr Val Asn Phe Thr Ile Phe
        275                 280                 285
Lys Val Arg Met Tyr Val Gly Gly Val Glu His Arg Leu Glu Ala Ala
    290                 295                 300
Cys Asn Trp Thr Arg Gly Glu Arg Cys Asp Leu Glu Asp Arg Asp Arg
305                 310                 315                 320
Ser Glu Leu Ser Pro Leu Leu Leu Ser Thr Thr Glu Trp Gln Val Leu
                325                 330                 335
Pro Cys Ser Phe Thr Thr Leu Pro Ala Leu Ser Thr Gly Leu Ile His
            340                 345                 350
Leu His Gln Asn Ile Val Asp Val Gln Tyr Leu Tyr Gly Ile Gly Ser
        355                 360                 365
Ala Val Val Ser Phe Ala Ile Lys Trp Glu Tyr Ile Leu Leu Leu Phe
    370                 375                 380
Leu Leu Leu Ala Asp Ala Arg Val Cys Ala Cys Leu Trp Met Met Leu
385                 390                 395                 400
Leu Ile
```

( 2 ) INFORMATION FOR SEQ ID NO:5:

( i ) SEQUENCE CHARACTERISTICS:
        ( A ) LENGTH: 402 amino acids ( B ) TYPE: amino acid
( D ) TOPOLOGY: unknown ( i i ) MOLECULE TYPE: protein ( v i ) ORIGINAL SOURCE:
( A ) ORGANISM: Hepatitis C virus ( v i i ) IMMEDIATE SOURCE:
( B ) CLONE: N27,N19,H19,Y19,MX24

( x i ) SEQUENCE DESCRIPTION: SEQ ID NO:5:

| Ile | Pro | Gln | Ala | Val | Val | Asp | Met | Val | Ala | Gly | Ala | His | Trp | Gly | Val |
|---|---|---|---|---|---|---|---|---|---|---|---|---|---|---|---|
| 1 | | | | 5 | | | | | 10 | | | | | 15 | |
| Leu | Ala | Gly | Leu | Ala | Tyr | Tyr | Ser | Met | Val | Gly | Asn | Trp | Ala | Lys | Val |
| | | | 20 | | | | | 25 | | | | | 30 | | |
| Leu | Val | Val | Met | Leu | Leu | Phe | Ala | Gly | Val | Asp | Gly | Xaa | Thr | His | Val |
| | | | 35 | | | | 40 | | | | | 45 | | | |
| Thr | Gly | Gly | Lys | Val | Ala | Tyr | Thr | Thr | Gln | Xaa | Phe | Thr | Xaa | Phe | Phe |
| | 50 | | | | | 55 | | | | | 60 | | | | |
| Ser | Arg | Gly | Pro | Ser | Gln | Xaa | Ile | Gln | Leu | Val | Asn | Thr | Asn | Gly | Ser |
| 65 | | | | | 70 | | | | | 75 | | | | | 80 |
| Trp | His | Ile | Asn | Arg | Thr | Ala | Leu | Asn | Cys | Asn | Asp | Ser | Leu | Xaa | Thr |
| | | | | 85 | | | | | 90 | | | | | 95 | |
| Gly | Phe | Leu | Ala | Xaa | Leu | Phe | Tyr | Xaa | His | Ser | Phe | Xaa | Ala | Ser | Gly |
| | | | 100 | | | | | 105 | | | | | 110 | | |
| Cys | Pro | Glu | Arg | Met | Ala | Xaa | Cys | Arg | Pro | Ile | Xaa | Glu | Phe | Ala | Gln |
| | | | | 115 | | | | | 120 | | | | | 125 | |
| Gly | Trp | Xaa | Pro | Ile | Thr | His | Val | Val | Pro | Xaa | Xaa | Ser | Asp | Gln | Arg |
| | | 130 | | | | | 135 | | | | | 140 | | | |
| Pro | Tyr | Cys | Trp | His | Tyr | Ala | Pro | Arg | Pro | Cys | Gly | Xaa | Val | Pro | Ala |
| 145 | | | | | 150 | | | | | 155 | | | | | 160 |
| Xaa | Gln | Val | Cys | Gly | Pro | Val | Tyr | Cys | Phe | Thr | Pro | Ser | Pro | Val | Val |
| | | | | 165 | | | | | 170 | | | | | 175 | |
| Val | Gly | Thr | Thr | Asp | Arg | Xaa | Gly | Ala | Pro | Thr | Tyr | Xaa | Trp | Gly | Xaa |
| | | | 180 | | | | | 185 | | | | | 190 | | |
| Asn | Glu | Thr | Asp | Val | Leu | Leu | Leu | Asn | Asn | Thr | Arg | Pro | Pro | Gln | Gly |
| | | | 195 | | | | | 200 | | | | | 205 | | |
| Asn | Trp | Phe | Gly | Cys | Thr | Trp | Met | Asn | Gly | Thr | Gly | Phe | Thr | Lys | Thr |
| | | 210 | | | | | 215 | | | | | 220 | | | |
| Cys | Gly | Gly | Pro | Pro | Cys | Asn | Ile | Gly | Gly | Val | Gly | Asn | Asn | Thr | Leu |
| 225 | | | | | 230 | | | | | 235 | | | | | 240 |
| Thr | Cys | Pro | Thr | Asp | Cys | Phe | Arg | Lys | His | Pro | Glu | Ala | Thr | Tyr | Thr |
| | | | | 245 | | | | | 250 | | | | | 255 | |
| Lys | Cys | Gly | Ser | Gly | Pro | Trp | Leu | Thr | Pro | Arg | Cys | Leu | Val | His | Tyr |
| | | | 260 | | | | | 265 | | | | | 270 | | |
| Pro | Tyr | Arg | Leu | Trp | His | Tyr | Pro | Cys | Thr | Val | Asn | Phe | Thr | Ile | Phe |
| | | 275 | | | | | 280 | | | | | 285 | | | |
| Lys | Val | Arg | Met | Tyr | Val | Gly | Gly | Val | Glu | His | Arg | Leu | Glu | Ala | Ala |
| | 290 | | | | | 295 | | | | | 300 | | | | |
| Cys | Asn | Trp | Thr | Arg | Gly | Glu | Arg | Cys | Asp | Leu | Glu | Asp | Arg | Asp | Arg |
| 305 | | | | | 310 | | | | | 315 | | | | | 320 |
| Ser | Glu | Leu | Ser | Pro | Leu | Leu | Leu | Ser | Thr | Thr | Glu | Trp | Gln | Val | Leu |
| | | | | 325 | | | | | 330 | | | | | 335 | |
| Pro | Cys | Ser | Phe | Thr | Thr | Leu | Pro | Ala | Leu | Ser | Thr | Gly | Leu | Ile | His |
| | | | 340 | | | | | 345 | | | | | 350 | | |
| Leu | His | Gln | Asn | Ile | Val | Asp | Val | Gln | Tyr | Leu | Tyr | Gly | Ile | Gly | Ser |

```
                       355                        360                             365
         Ala Val Val Ser Phe Ala Ile Lys Trp Glu Tyr Ile Leu Leu Leu Phe
             370                     375                 380
         Leu Leu Leu Ala Asp Ala Arg Val Cys Ala Cys Leu Trp Met Met Leu
         385                     390                 395                     400
         Leu Ile
```

( 2 ) INFORMATION FOR SEQ ID NO:6:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Hepatitis C virus ( v i i ) IMMEDIATE SOURCE:
        ( B ) CLONE: BK164

( i x ) FEATURE:
        ( A ) NAME/KEY: CDS
        ( B ) LOCATION: 2..1207

( x i ) SEQUENCE DESCRIPTION: SEQ ID NO:6:

```
G ATC CCA CAA GCC GTC GTG GAC ATG GTG GCG GGG GCC CAC TGG GGA            46
  Ile Pro Gln Ala Val Val Asp Met Val Ala Gly Ala His Trp Gly
  1               5                   10                  15

GTC CTG GCG GGC CTT GCC TAC TAT TCC ATG GCG GGG AAC TGG GCT AAG          94
Val Leu Ala Gly Leu Ala Tyr Tyr Ser Met Ala Gly Asn Trp Ala Lys
                20                  25                  30

GTT CTG ATT GTG ATG CTA CTT TTT GCT GGC GTT GAC GGG GAT ACC CAC          142
Val Leu Ile Val Met Leu Leu Phe Ala Gly Val Asp Gly Asp Thr His
                35              40                  45

GTG ACA GGG GGG GCG CAA GCC AAA ACC ACC AAC AGG CTC GTG TCC ATG          190
Val Thr Gly Gly Ala Gln Ala Lys Thr Thr Asn Arg Leu Val Ser Met
            50              55                  60

TTC GCA AGT GGG CCG TCT CAG AAA ATC CAG CTT ATA AAC ACC AAT GGG          238
Phe Ala Ser Gly Pro Ser Gln Lys Ile Gln Leu Ile Asn Thr Asn Gly
        65              70                  75

AGT TGG CAC ATC AAC AGG ACT GCC CTG AAC TGC AAT GAC TCT CTC CAG          286
Ser Trp His Ile Asn Arg Thr Ala Leu Asn Cys Asn Asp Ser Leu Gln
80              85                  90                      95

ACT GGG TTT CTT GCC GCG CTG TTC TAC ACA CAT AGT TTC AAC TCG TCC          334
Thr Gly Phe Leu Ala Ala Leu Phe Tyr Thr His Ser Phe Asn Ser Ser
                100                 105                 110

GGG TGC CCA GAG CGC ATG GCC CAG TGC CGC ACC ATT GAC AAG TTC GAC          382
Gly Cys Pro Glu Arg Met Ala Gln Cys Arg Thr Ile Asp Lys Phe Asp
            115                 120                 125

CAG GGA TGG GGT CCC ATT ACT TAT GCT GAG TCT AGC AGA TCA GAC CAG          430
Gln Gly Trp Gly Pro Ile Thr Tyr Ala Glu Ser Ser Arg Ser Asp Gln
        130                 135                 140

AGG CCA TAT TGC TGG CAC TAC CCA CCT CCA CAA TGT ACC ATC GTA CCT          478
Arg Pro Tyr Cys Trp His Tyr Pro Pro Pro Gln Cys Thr Ile Val Pro
145                 150                 155

GCG TCG GAG GTG TGC GGC CCA GTG TAC TGC TTC ACC CCA AGC CCT GTC          526
Ala Ser Glu Val Cys Gly Pro Val Tyr Cys Phe Thr Pro Ser Pro Val
160                 165                 170                 175

GTC GTG GGG ACG ACC GAT CGT TTC GGT GTC CCT ACG TAT AGA TGG GGG          574
```

| | | | | | | | | | | | | | | | | |
|---|---|---|---|---|---|---|---|---|---|---|---|---|---|---|---|---|
|Val|Val|Gly|Thr|Thr|Asp|Arg|Phe|Gly|Val|Pro|Thr|Tyr|Arg|Trp|Gly| |
| | | |180| | | | |185| | | | |190| | | |
|GAG|AAC|GAG|ACT|GAC|GTG|CTG|CTG|CTC|AAC|AAC|ACG|CGG|CCG|CCG|CAA|622|
|Glu|Asn|Glu|Thr|Asp|Val|Leu|Leu|Leu|Asn|Asn|Thr|Arg|Pro|Pro|Gln| |
| | | |195| | | | |200| | | | |205| | | |
|GGC|AAC|TGG|TTC|GGC|TGC|ACA|TGG|ATG|AAT|AGC|ACC|GGG|TTC|ACC|AAG|670|
|Gly|Asn|Trp|Phe|Gly|Cys|Thr|Trp|Met|Asn|Ser|Thr|Gly|Phe|Thr|Lys| |
| | | |210| | | | |215| | | | |220| | | |
|ACA|TGT|GGG|GGG|CCC|CCC|TGT|AAC|ATC|GGG|GGG|GTC|GGC|AAC|AAC|ACC|718|
|Thr|Cys|Gly|Gly|Pro|Pro|Cys|Asn|Ile|Gly|Gly|Val|Gly|Asn|Asn|Thr| |
| |225| | | | |230| | | | |235| | | | | |
|CTG|ACC|TGC|CCC|ACG|GAC|TGC|TTC|CGG|AAG|CAC|CCC|GAG|GCT|ACC|TAC|766|
|Leu|Thr|Cys|Pro|Thr|Asp|Cys|Phe|Arg|Lys|His|Pro|Glu|Ala|Thr|Tyr| |
|240| | | | |245| | | | |250| | | | |255| |
|ACA|AAA|TGT|GGT|TCG|GGG|CCT|TGG|CTG|ACA|CCT|AGG|TGC|ATG|GTT|GAC|814|
|Thr|Lys|Cys|Gly|Ser|Gly|Pro|Trp|Leu|Thr|Pro|Arg|Cys|Met|Val|Asp| |
| | | | |260| | | | |265| | | | |270| | |
|TAT|CCA|TAC|AGG|CTC|TGG|CAT|TAC|CCC|TGC|ACT|GTT|AAC|TTT|ACC|ATC|862|
|Tyr|Pro|Tyr|Arg|Leu|Trp|His|Tyr|Pro|Cys|Thr|Val|Asn|Phe|Thr|Ile| |
| | | |275| | | | |280| | | | |285| | | |
|TTC|AAG|GTT|AGG|ATG|TAT|GTG|GGG|GGG|GTG|GAG|GAC|AGG|CTC|AAT|GCT|910|
|Phe|Lys|Val|Arg|Met|Tyr|Val|Gly|Gly|Val|Glu|Asp|Arg|Leu|Asn|Ala| |
| | | |290| | | | |295| | | | |300| | | |
|GCA|TGC|AAT|TGG|ACC|CGA|GGA|GAG|CGT|TGT|GAC|TTG|GAG|GAC|AGG|GAT|958|
|Ala|Cys|Asn|Trp|Thr|Arg|Gly|Glu|Arg|Cys|Asp|Leu|Glu|Asp|Arg|Asp| |
| |305| | | | |310| | | | |315| | | | | |
|AGG|CCG|GAG|CTC|AGC|CCG|CTG|CTG|CTG|TCT|ACA|ACA|GAG|TGG|CAG|GTA|1006|
|Arg|Pro|Glu|Leu|Ser|Pro|Leu|Leu|Leu|Ser|Thr|Thr|Glu|Trp|Gln|Val| |
|320| | | | |325| | | | |330| | | | |335| |
|CTG|CCC|TGT|TCC|TTC|ACC|ACC|CTA|CCA|GCT|CTG|TCC|ACT|GGC|TTG|ATT|1054|
|Leu|Pro|Cys|Ser|Phe|Thr|Thr|Leu|Pro|Ala|Leu|Ser|Thr|Gly|Leu|Ile| |
| | | | |340| | | | |345| | | | |350| | |
|CAC|CTC|CAT|CAG|AAC|ATC|GTG|GAC|GTG|CAA|TAC|CTA|TAC|GGT|ATA|GGG|1102|
|His|Leu|His|Gln|Asn|Ile|Val|Asp|Val|Gln|Tyr|Leu|Tyr|Gly|Ile|Gly| |
| | | |355| | | | |360| | | | |365| | | |
|TCA|GCG|GTT|GTC|TCC|TTT|GCA|ATC|AAA|TGG|GAG|TAT|GTC|CTG|TTG|CTT|1150|
|Ser|Ala|Val|Val|Ser|Phe|Ala|Ile|Lys|Trp|Glu|Tyr|Val|Leu|Leu|Leu| |
| | | |370| | | | |375| | | | |380| | | |
|TTC|CTT|CTC|CTA|GCG|GAC|GCA|CGT|GTC|TGT|GCC|TGC|TTG|TGG|ATG|ATG|1198|
|Phe|Leu|Leu|Leu|Ala|Asp|Ala|Arg|Val|Cys|Ala|Cys|Leu|Trp|Met|Met| |
| |385| | | | |390| | | | |395| | | | | |
|CTG|CTG|ATA| | | | | | | | | | | | | |1207|
|Leu|Leu|Ile| | | | | | | | | | | | | | |
|400| | | | | | | | | | | | | | | | |

( 2 ) INFORMATION FOR SEQ ID NO:7:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
|Ile|Pro|Gln|Ala|Val|Val|Asp|Met|Val|Ala|Gly|Ala|His|Trp|Gly|Val|
|1| | | |5| | | | |10| | | | |15| |
|Leu|Ala|Gly|Leu|Ala|Tyr|Tyr|Ser|Met|Ala|Gly|Asn|Trp|Ala|Lys|Val|
| | | | |20| | | | |25| | | | |30| |
|Leu|Ile|Val|Met|Leu|Leu|Phe|Ala|Gly|Val|Asp|Gly|Asp|Thr|His|Val|
| | | | |35| | | | |40| | | | |45| |

```
Thr  Gly  Gly  Ala  Gln  Ala  Lys  Thr  Thr  Asn  Arg  Leu  Val  Ser  Met  Phe
     50                  55                       60
Ala  Ser  Gly  Pro  Ser  Gln  Lys  Ile  Gln  Leu  Ile  Asn  Thr  Asn  Gly  Ser
65                       70                  75                            80
Trp  His  Ile  Asn  Arg  Thr  Ala  Leu  Asn  Cys  Asn  Asp  Ser  Leu  Gln  Thr
               85                       90                       95
Gly  Phe  Leu  Ala  Ala  Leu  Phe  Tyr  Thr  His  Ser  Phe  Asn  Ser  Ser  Gly
               100                      105                      110
Cys  Pro  Glu  Arg  Met  Ala  Gln  Cys  Arg  Thr  Ile  Asp  Lys  Phe  Asp  Gln
          115                      120                 125
Gly  Trp  Gly  Pro  Ile  Thr  Tyr  Ala  Glu  Ser  Ser  Arg  Ser  Asp  Gln  Arg
     130                      135                      140
Pro  Tyr  Cys  Trp  His  Tyr  Pro  Pro  Pro  Gln  Cys  Thr  Ile  Val  Pro  Ala
145                      150                      155                      160
Ser  Glu  Val  Cys  Gly  Pro  Val  Tyr  Cys  Phe  Thr  Pro  Ser  Pro  Val  Val
                165                      170                      175
Val  Gly  Thr  Thr  Asp  Arg  Phe  Gly  Val  Pro  Thr  Tyr  Arg  Trp  Gly  Glu
               180                      185                 190
Asn  Glu  Thr  Asp  Val  Leu  Leu  Leu  Asn  Asn  Thr  Arg  Pro  Pro  Gln  Gly
          195                      200                 205
Asn  Trp  Phe  Gly  Cys  Thr  Trp  Met  Asn  Ser  Thr  Gly  Phe  Thr  Lys  Thr
     210                      215                 220
Cys  Gly  Gly  Pro  Pro  Cys  Asn  Ile  Gly  Gly  Val  Gly  Asn  Asn  Thr  Leu
225                      230                 235                           240
Thr  Cys  Pro  Thr  Asp  Cys  Phe  Arg  Lys  His  Pro  Glu  Ala  Thr  Tyr  Thr
               245                      250                      255
Lys  Cys  Gly  Ser  Gly  Pro  Trp  Leu  Thr  Pro  Arg  Cys  Met  Val  Asp  Tyr
          260                      265                      270
Pro  Tyr  Arg  Leu  Trp  His  Tyr  Pro  Cys  Thr  Val  Asn  Phe  Thr  Ile  Phe
          275                      280                 285
Lys  Val  Arg  Met  Tyr  Val  Gly  Gly  Val  Glu  Asp  Arg  Leu  Asn  Ala  Ala
     290                      295                 300
Cys  Asn  Trp  Thr  Arg  Gly  Glu  Arg  Cys  Asp  Leu  Glu  Asp  Arg  Asp  Arg
305                      310                 315                           320
Pro  Glu  Leu  Ser  Pro  Leu  Leu  Leu  Ser  Thr  Thr  Glu  Trp  Gln  Val  Leu
                325                      330                      335
Pro  Cys  Ser  Phe  Thr  Thr  Leu  Pro  Ala  Leu  Ser  Thr  Gly  Leu  Ile  His
               340                      345                 350
Leu  His  Gln  Asn  Ile  Val  Asp  Val  Gln  Tyr  Leu  Tyr  Gly  Ile  Gly  Ser
          355                      360                 365
Ala  Val  Val  Ser  Phe  Ala  Ile  Lys  Trp  Glu  Tyr  Val  Leu  Leu  Leu  Phe
     370                      375                 380
Leu  Leu  Leu  Ala  Asp  Ala  Arg  Val  Cys  Ala  Cys  Leu  Trp  Met  Met  Leu
385                      390                      395                      400
Leu  Ile
```

( 2 ) INFORMATION FOR SEQ ID NO:8:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO (vi) ORIGINAL SOURCE:
 (A) ORGANISM: Hepatitis C virus (vii) IMMEDIATE SOURCE:
 (B) CLONE: HCV-J (ix) FEATURE:
 (A

| | | | | | | | | | | | | | | | |
|---|---|---|---|---|---|---|---|---|---|---|---|---|---|---|---|
| TAC | CCA | TAC | AGG | CTC | TGG | CAC | TAC | CCC | TGC | ACT | GTT | AAC | TTT | ACC | GTC |
| Tyr | Pro | Tyr | Arg | Leu | Trp | His | Tyr | Pro | Cys | Thr | Val | Asn | Phe | Thr | Val |
|  |  |  | 275 |  |  |  | 280 |  |  |  |  |  | 285 |  |  |

862

| TTT | AAG | GTC | AGG | ATG | TAT | GTG | GGG | GGC | GTG | GAG | CAC | AGG | CTC | AAT | GCT |
|---|---|---|---|---|---|---|---|---|---|---|---|---|---|---|---|
| Phe | Lys | Val | Arg | Met | Tyr | Val | Gly | Gly | Val | Glu | His | Arg | Leu | Asn | Ala |
|  |  | 290 |  |  |  |  | 295 |  |  |  |  | 300 |  |  |  |

910

| GCA | TGC | AAT | TGG | ACT | CGA | GGA | GAG | CGC | TGT | GAC | TTG | GAG | GAC | AGG | GAT |
|---|---|---|---|---|---|---|---|---|---|---|---|---|---|---|---|
| Ala | Cys | Asn | Trp | Thr | Arg | Gly | Glu | Arg | Cys | Asp | Leu | Glu | Asp | Arg | Asp |
|  |  | 305 |  |  |  |  | 310 |  |  |  |  | 315 |  |  |  |

958

| AGG | TCA | GAA | CTC | AGC | CCG | CTG | CTG | CTG | TCT | ACA | ACA | GAG | TGG | CAG | ATA |
|---|---|---|---|---|---|---|---|---|---|---|---|---|---|---|---|
| Arg | Ser | Glu | Leu | Ser | Pro | Leu | Leu | Leu | Ser | Thr | Thr | Glu | Trp | Gln | Ile |
| 320 |  |  |  |  | 325 |  |  |  |  | 330 |  |  |  |  | 335 |

1006

| CTG | CCC | TGT | TCC | TTC | ACC | ACC | CTA | CCG | GCC | CTG | TCC | ACT | GGC | TTG | ATC |
|---|---|---|---|---|---|---|---|---|---|---|---|---|---|---|---|
| Leu | Pro | Cys | Ser | Phe | Thr | Thr | Leu | Pro | Ala | Leu | Ser | Thr | Gly | Leu | Ile |
|  |  |  |  | 340 |  |  |  |  | 345 |  |  |  |  | 350 |  |

1054

| CAT | CTT | CAC | CGG | AAC | ATC | GTG | GAC | GTG | CAA | TAC | CTG | TAC | GGT | ATA | GGG |
|---|---|---|---|---|---|---|---|---|---|---|---|---|---|---|---|
| His | Leu | His | Arg | Asn | Ile | Val | Asp | Val | Gln | Tyr | Leu | Tyr | Gly | Ile | Gly |
|  |  |  | 355 |  |  |  |  | 360 |  |  |  |  | 365 |  |  |

1102

| TCG | GCA | GTT | GTC | TCC | TTT | GCA | ATC | AAA | TGG | GAG | TAT | ATC | CTG | TTG | CTT |
|---|---|---|---|---|---|---|---|---|---|---|---|---|---|---|---|
| Ser | Ala | Val | Val | Ser | Phe | Ala | Ile | Lys | Trp | Glu | Tyr | Ile | Leu | Leu | Leu |
|  |  | 370 |  |  |  |  | 375 |  |  |  |  | 380 |  |  |  |

1150

| TTC | CTT | CTT | CTG | GCG | GAC | GCG | CGC | GTC | TGT | GCC | TGC | TTG | TGG | ATG | ATG |
|---|---|---|---|---|---|---|---|---|---|---|---|---|---|---|---|
| Phe | Leu | Leu | Leu | Ala | Asp | Ala | Arg | Val | Cys | Ala | Cys | Leu | Trp | Met | Met |
| 385 |  |  |  |  | 390 |  |  |  |  | 395 |  |  |  |  |  |

1198

| CTG | CTG | ATA |
|---|---|---|
| Leu | Leu | Ile |
| 400 |  |  |

1207

( 2 ) INFORMATION FOR SEQ ID NO:9:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Ile | Pro | Gln | Ala | Val | Val | Asp | Met | Val | Ala | Gly | Ala | His | Trp | Gly | Val |
|---|---|---|---|---|---|---|---|---|---|---|---|---|---|---|---|
| 1 |  |  |  | 5 |  |  |  |  | 10 |  |  |  |  | 15 |  |

| Leu | Ala | Gly | Leu | Ala | Tyr | Tyr | Ser | Met | Val | Gly | Asn | Trp | Ala | Lys | Val |
|---|---|---|---|---|---|---|---|---|---|---|---|---|---|---|---|
|  |  |  | 20 |  |  |  |  | 25 |  |  |  |  | 30 |  |  |

| Leu | Ile | Val | Met | Leu | Leu | Phe | Ala | Gly | Val | Asp | Gly | His | Thr | His | Val |
|---|---|---|---|---|---|---|---|---|---|---|---|---|---|---|---|
|  |  |  | 35 |  |  |  |  | 40 |  |  |  |  | 45 |  |  |

| Thr | Gly | Gly | Arg | Val | Ala | Ser | Ser | Thr | Gln | Ser | Leu | Val | Ser | Trp | Leu |
|---|---|---|---|---|---|---|---|---|---|---|---|---|---|---|---|
|  | 50 |  |  |  |  | 55 |  |  |  |  | 60 |  |  |  |  |

| Ser | Gln | Gly | Pro | Ser | Gln | Lys | Ile | Gln | Leu | Val | Asn | Thr | Asn | Gly | Ser |
|---|---|---|---|---|---|---|---|---|---|---|---|---|---|---|---|
| 65 |  |  |  |  | 70 |  |  |  |  | 75 |  |  |  |  | 80 |

| Trp | His | Ile | Asn | Arg | Thr | Ala | Leu | Asn | Cys | Asn | Asp | Ser | Leu | Gln | Thr |
|---|---|---|---|---|---|---|---|---|---|---|---|---|---|---|---|
|  |  |  |  | 85 |  |  |  |  | 90 |  |  |  |  | 95 |  |

| Gly | Phe | Ile | Ala | Ala | Leu | Phe | Tyr | Ala | His | Arg | Phe | Asn | Ala | Ser | Gly |
|---|---|---|---|---|---|---|---|---|---|---|---|---|---|---|---|
|  |  |  | 100 |  |  |  |  | 105 |  |  |  |  | 110 |  |  |

| Cys | Pro | Glu | Arg | Met | Ala | Ser | Cys | Arg | Pro | Ile | Asp | Glu | Phe | Ala | Gln |
|---|---|---|---|---|---|---|---|---|---|---|---|---|---|---|---|
|  |  | 115 |  |  |  |  | 120 |  |  |  |  | 125 |  |  |  |

| Gly | Trp | Gly | Pro | Ile | Thr | His | Asp | Met | Pro | Glu | Ser | Ser | Asp | Gln | Arg |
|---|---|---|---|---|---|---|---|---|---|---|---|---|---|---|---|
|  | 130 |  |  |  |  | 135 |  |  |  |  | 140 |  |  |  |  |

| Pro | Tyr | Cys | Trp | His | Tyr | Ala | Pro | Arg | Pro | Cys | Gly | Ile | Val | Pro | Ala |
|---|---|---|---|---|---|---|---|---|---|---|---|---|---|---|---|
| 145 |  |  |  |  | 150 |  |  |  |  | 155 |  |  |  |  | 160 |

| Ser | Gln | Val | Cys | Gly | Pro | Val | Tyr | Cys | Phe | Thr | Pro | Ser | Pro | Val | Val |
|---|---|---|---|---|---|---|---|---|---|---|---|---|---|---|---|

|   |   |   |   |   |   |   |   |   | 165 |   |   |   |   | 170 |   |   |   |   | 175 |   |   |
|---|---|---|---|---|---|---|---|---|---|---|---|---|---|---|---|---|---|---|---|---|---|

Val Gly Thr Thr Asp Arg Phe Gly Ala Pro Thr Tyr Ser Trp Gly Glu
                        180                 185                 190

Asn Glu Thr Asp Val Leu Leu Leu Ser Asn Thr Arg Pro Pro Gln Gly
        195                     200                 205

Asn Trp Phe Gly Cys Thr Trp Met Asn Ser Thr Gly Phe Thr Lys Thr
    210                 215                 220

Cys Gly Gly Pro Pro Cys Asn Ile Gly Gly Val Gly Asn Asn Thr Leu
225                 230                 235                     240

Val Cys Pro Thr Asp Cys Phe Arg Lys His Pro Glu Ala Thr Tyr Thr
                245                 250                 255

Lys Cys Gly Ser Gly Pro Trp Leu Thr Pro Arg Cys Met Val Asp Tyr
            260                 265                 270

Pro Tyr Arg Leu Trp His Tyr Pro Cys Thr Val Asn Phe Thr Val Phe
        275                 280                 285

Lys Val Arg Met Tyr Val Gly Gly Val Glu His Arg Leu Asn Ala Ala
    290                 295                 300

Cys Asn Trp Thr Arg Gly Glu Arg Cys Asp Leu Glu Asp Arg Asp Arg
305                 310                 315                     320

Ser Glu Leu Ser Pro Leu Leu Leu Ser Thr Thr Glu Trp Gln Ile Leu
                325                 330                 335

Pro Cys Ser Phe Thr Thr Leu Pro Ala Leu Ser Thr Gly Leu Ile His
            340                 345                 350

Leu His Arg Asn Ile Val Asp Val Gln Tyr Leu Tyr Gly Ile Gly Ser
        355                 360                 365

Ala Val Val Ser Phe Ala Ile Lys Trp Glu Tyr Ile Leu Leu Leu Phe
    370                 375                 380

Leu Leu Leu Ala Asp Ala Arg Val Cys Ala Cys Leu Trp Met Met Leu
385                 390                 395                     400

Leu Ile ( 2 ) INFORMATION FOR SEQ ID NO:10:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Hepatitis C virus ( v i i ) IMMEDIATE SOURCE:
        ( B ) CLONE: HCV-RNA33

( i x ) FEATURE:
        ( A ) NAME/KEY: CDS
        ( B ) LOCATION: 2..1207

( x i ) SEQUENCE DESCRIPTION: SEQ ID NO:10:

```
G ATC CCG CAA GCT GTC GTG GAC ATG GTG GCG GGG GCC CAC TGG GGA        46
  Ile Pro Gln Ala Val Val Asp Met Val Ala Gly Ala His Trp Gly
  1               5                   10                  15

GTC CTG GCG GGC CTG GCC TAC TAT TCC ATG GTG GGG AAC TGG GCT AAG      94
Val Leu Ala Gly Leu Ala Tyr Tyr Ser Met Val Gly Asn Trp Ala Lys
                20                  25                  30

GTT TTG ATT GTG ATG CTA CTC TTT GCC GGC GTT GAC GGG CAA ACC TAT     142
```

-continued

| | | | | | | | | | | | | | | | |
|---|---|---|---|---|---|---|---|---|---|---|---|---|---|---|---|
| Val | Leu | Ile | Val | Met | Leu | Leu | Phe | Ala | Gly | Val | Asp | Gly | Gln | Thr | Tyr |
| | | | 35 | | | | | 40 | | | | | 45 | | |

| ACG | ACG | GGG | GGG | GCG | GTT | GCC | CGC | ACC | ACC | ACC | GGG | TTC | GCG | TCC | CTC | 190 |
|---|---|---|---|---|---|---|---|---|---|---|---|---|---|---|---|---|
| Thr | Thr | Gly | Gly | Ala | Val | Ala | Arg | Thr | Thr | Thr | Gly | Phe | Ala | Ser | Leu | |
| | | 50 | | | | 55 | | | | | 60 | | | | | |

| TTC | TCC | GCT | GGG | TCG | CAG | GAG | AAC | ATC | CAG | CTT | ATA | AAC | ACC | AAT | GGC | 238 |
|---|---|---|---|---|---|---|---|---|---|---|---|---|---|---|---|---|
| Phe | Ser | Ala | Gly | Ser | Gln | Glu | Asn | Ile | Gln | Leu | Ile | Asn | Thr | Asn | Gly | |
| | 65 | | | | | 70 | | | | | 75 | | | | | |

| AGC | TGG | CAC | ATC | AAC | AGG | ACT | GCC | CTG | AAC | TGC | AAC | GAC | TCC | CTC | AAC | 286 |
|---|---|---|---|---|---|---|---|---|---|---|---|---|---|---|---|---|
| Ser | Trp | His | Ile | Asn | Arg | Thr | Ala | Leu | Asn | Cys | Asn | Asp | Ser | Leu | Asn | |
| 80 | | | | | 85 | | | | | 90 | | | | | 95 | |

| ACT | GGA | TTT | CTT | GCC | GCG | CTG | TTC | TAC | ACA | CAC | AAG | TTC | AAC | TCA | TCC | 334 |
|---|---|---|---|---|---|---|---|---|---|---|---|---|---|---|---|---|
| Thr | Gly | Phe | Leu | Ala | Ala | Leu | Phe | Tyr | Thr | His | Lys | Phe | Asn | Ser | Ser | |
| | | | | 100 | | | | | 105 | | | | | 110 | | |

| AGA | GCC | GAG | AGC | GTA | TTG | GCC | AGC | TGC | CGC | TTC | ATC | GAC | GAG | TTC | GAT | 382 |
|---|---|---|---|---|---|---|---|---|---|---|---|---|---|---|---|---|
| Arg | Ala | Glu | Ser | Val | Leu | Ala | Ser | Cys | Arg | Phe | Ile | Asp | Glu | Phe | Asp | |
| | | | 115 | | | | | 120 | | | | | 125 | | | |

| CAG | GGA | TGG | GGC | CCC | ATC | ACT | TAC | ACC | GAG | CGT | AAC | AGT | TCG | GAC | CAG | 430 |
|---|---|---|---|---|---|---|---|---|---|---|---|---|---|---|---|---|
| Gln | Gly | Trp | Gly | Pro | Ile | Thr | Tyr | Thr | Glu | Arg | Asn | Ser | Ser | Asp | Gln | |
| | | | 130 | | | | | 135 | | | | | 140 | | | |

| AGG | CCT | TAT | TGC | TGG | CAC | TAT | CCA | CCC | CGA | CAG | TGT | GGT | ATC | ATA | CCC | 478 |
|---|---|---|---|---|---|---|---|---|---|---|---|---|---|---|---|---|
| Arg | Pro | Tyr | Cys | Trp | His | Tyr | Pro | Pro | Arg | Gln | Cys | Gly | Ile | Ile | Pro | |
| | 145 | | | | | 150 | | | | | 155 | | | | | |

| GCG | TCG | GAG | GTG | TGC | GGT | CCA | GTG | TAT | TGT | TTC | ACC | CCA | AGC | CCT | GTT | 526 |
|---|---|---|---|---|---|---|---|---|---|---|---|---|---|---|---|---|
| Ala | Ser | Glu | Val | Cys | Gly | Pro | Val | Tyr | Cys | Phe | Thr | Pro | Ser | Pro | Val | |
| 160 | | | | | 165 | | | | | 170 | | | | | 175 | |

| GTG | GTG | GGG | ACA | ACC | GAT | CGG | TTC | GGT | GTC | CCT | ACA | TAC | AGC | TGG | GGG | 574 |
|---|---|---|---|---|---|---|---|---|---|---|---|---|---|---|---|---|
| Val | Val | Gly | Thr | Thr | Asp | Arg | Phe | Gly | Val | Pro | Thr | Tyr | Ser | Trp | Gly | |
| | | | | 180 | | | | | 185 | | | | | 190 | | |

| GAG | AAT | GAG | ACG | GAC | GTG | CTG | GTT | CTC | AAC | AAC | ACG | CGG | CCG | CCG | CAG | 622 |
|---|---|---|---|---|---|---|---|---|---|---|---|---|---|---|---|---|
| Glu | Asn | Glu | Thr | Asp | Val | Leu | Val | Leu | Asn | Asn | Thr | Arg | Pro | Pro | Gln | |
| | | | 195 | | | | | 200 | | | | | 205 | | | |

| GGC | AAC | TGG | TTC | GGC | TGT | ACA | TGG | ATG | AAT | GGC | ACT | GGT | TTC | ACC | AAG | 670 |
|---|---|---|---|---|---|---|---|---|---|---|---|---|---|---|---|---|
| Gly | Asn | Trp | Phe | Gly | Cys | Thr | Trp | Met | Asn | Gly | Thr | Gly | Phe | Thr | Lys | |
| | | 210 | | | | | 215 | | | | | 220 | | | | |

| ACA | TGC | GGG | GGT | CCC | CCG | TGT | CAC | ATC | GGG | GGG | CGC | GGC | AAC | AAC | ACC | 718 |
|---|---|---|---|---|---|---|---|---|---|---|---|---|---|---|---|---|
| Thr | Cys | Gly | Gly | Pro | Pro | Cys | His | Ile | Gly | Gly | Arg | Gly | Asn | Asn | Thr | |
| | 225 | | | | | 230 | | | | | 235 | | | | | |

| CTG | ACT | TGC | CCC | ACG | GAC | TGC | TTC | CGG | AAG | CAT | CCC | GAG | GCT | ACG | TAT | 766 |
|---|---|---|---|---|---|---|---|---|---|---|---|---|---|---|---|---|
| Leu | Thr | Cys | Pro | Thr | Asp | Cys | Phe | Arg | Lys | His | Pro | Glu | Ala | Thr | Tyr | |
| 240 | | | | | 245 | | | | | 250 | | | | | 255 | |

| ACA | AAA | TGT | GGT | TCG | GGG | CCT | TGG | TTG | ACA | CCT | AGG | TGC | ATG | GTT | GAT | 814 |
|---|---|---|---|---|---|---|---|---|---|---|---|---|---|---|---|---|
| Thr | Lys | Cys | Gly | Ser | Gly | Pro | Trp | Leu | Thr | Pro | Arg | Cys | Met | Val | Asp | |
| | | | | 260 | | | | | 265 | | | | | 270 | | |

| TAC | CCA | TAC | AGG | CTC | TGG | CAC | TAC | CCC | TGC | ACT | GTC | AAC | TTT | ACC | ACC | 862 |
|---|---|---|---|---|---|---|---|---|---|---|---|---|---|---|---|---|
| Tyr | Pro | Tyr | Arg | Leu | Trp | His | Tyr | Pro | Cys | Thr | Val | Asn | Phe | Thr | Thr | |
| | | | 275 | | | | | 280 | | | | | 285 | | | |

| TTT | AAG | GTT | AGG | ATG | TAT | GTG | GGG | GGC | GTG | GAG | CAC | AGG | CTC | ATT | GCT | 910 |
|---|---|---|---|---|---|---|---|---|---|---|---|---|---|---|---|---|
| Phe | Lys | Val | Arg | Met | Tyr | Val | Gly | Gly | Val | Glu | His | Arg | Leu | Ile | Ala | |
| | | 290 | | | | | 295 | | | | | 300 | | | | |

| GCA | TGC | AAT | TGG | ACT | CGA | GGA | GAC | CGT | TGT | AAC | TTG | GAG | GAC | AGG | GAT | 958 |
|---|---|---|---|---|---|---|---|---|---|---|---|---|---|---|---|---|
| Ala | Cys | Asn | Trp | Thr | Arg | Gly | Asp | Arg | Cys | Asn | Leu | Glu | Asp | Arg | Asp | |
| | 305 | | | | | 310 | | | | | 315 | | | | | |

| AGA | TCA | GAG | CTT | AGT | CCG | CTG | CTG | CTG | TCT | ACG | ACA | GAG | TGG | CAG | ATA | 1006 |
|---|---|---|---|---|---|---|---|---|---|---|---|---|---|---|---|---|
| Arg | Ser | Glu | Leu | Ser | Pro | Leu | Leu | Leu | Ser | Thr | Thr | Glu | Trp | Gln | Ile | |
| 320 | | | | | 325 | | | | | 330 | | | | | 335 | |

| CTG | CCC | TGT | TCC | TTC | ACC | ACC | CTA | CCG | GCT | CTC | TCC | ACC | GGT | TTG | ATC | 1054 |
|---|---|---|---|---|---|---|---|---|---|---|---|---|---|---|---|---|
| Leu | Pro | Cys | Ser | Phe | Thr | Thr | Leu | Pro | Ala | Leu | Ser | Thr | Gly | Leu | Ile | |
| | | | | 340 | | | | | 345 | | | | | 350 | | |

| CAT | CTC | CAT | CAG | AAC | ATC | GTG | GAC | GTG | CAA | TAC | CTG | TAC | GGT | ATA | GGG | 1102 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| His | Leu | His | Gln | Asn | Ile | Val | Asp | Val | Gln | Tyr | Leu | Tyr | Gly | Ile | Gly |      |
|     |     |     | 355 |     |     |     |     | 360 |     |     |     |     | 365 |     |     |      |
| TCT | GCT | GTT | GTC | TCC | ATT | GCA | ATC | AGG | TGG | GAA | TAT | GTC | CTG | TTG | CTT | 1150 |
| Ser | Ala | Val | Val | Ser | Ile | Ala | Ile | Arg | Trp | Glu | Tyr | Val | Leu | Leu | Leu |      |
|     |     | 370 |     |     |     | 375 |     |     |     |     | 380 |     |     |     |     |      |
| TTC | CTT | CTC | CTG | GCG | GAC | GCG | CGT | GTC | TGT | GCC | TGC | TTG | TGG | ATG | ATG | 1198 |
| Phe | Leu | Leu | Leu | Ala | Asp | Ala | Arg | Val | Cys | Ala | Cys | Leu | Trp | Met | Met |      |
|     | 385 |     |     |     |     | 390 |     |     |     |     | 395 |     |     |     |     |      |
| CTG | CTG | ATA |     |     |     |     |     |     |     |     |     |     |     |     |     | 1207 |
| Leu | Leu | Ile |     |     |     |     |     |     |     |     |     |     |     |     |     |      |
| 400 |     |     |     |     |     |     |     |     |     |     |     |     |     |     |     |      |

( 2 ) INFORMATION FOR SEQ ID NO:11:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

|     |     |     |     |     |     |     |     |     |     |     |     |     |     |     |
| --- | --- | --- | --- | --- | --- | --- | --- | --- | --- | --- | --- | --- | --- | --- |
| Ile | Pro | Gln | Ala | Val | Val | Asp | Met | Val | Ala | Gly | Ala | His | Trp | Gly | Val |
| 1   |     |     |     | 5   |     |     |     |     | 10  |     |     |     |     | 15  |
| Leu | Ala | Gly | Leu | Ala | Tyr | Tyr | Ser | Met | Val | Gly | Asn | Trp | Ala | Lys | Val |
|     |     |     | 20  |     |     |     |     | 25  |     |     |     |     | 30  |     |
| Leu | Ile | Val | Met | Leu | Leu | Phe | Ala | Gly | Val | Asp | Gly | Gln | Thr | Tyr | Thr |
|     |     | 35  |     |     |     |     | 40  |     |     |     |     | 45  |     |     |
| Thr | Gly | Gly | Ala | Val | Ala | Arg | Thr | Thr | Thr | Gly | Phe | Ala | Ser | Leu | Phe |
|     | 50  |     |     |     |     | 55  |     |     |     |     | 60  |     |     |     |
| Ser | Ala | Gly | Ser | Gln | Glu | Asn | Ile | Gln | Leu | Ile | Asn | Thr | Asn | Gly | Ser |
| 65  |     |     |     |     | 70  |     |     |     |     | 75  |     |     |     |     | 80  |
| Trp | His | Ile | Asn | Arg | Thr | Ala | Leu | Asn | Cys | Asn | Asp | Ser | Leu | Asn | Thr |
|     |     |     |     | 85  |     |     |     |     | 90  |     |     |     |     | 95  |     |
| Gly | Phe | Leu | Ala | Ala | Leu | Phe | Tyr | Thr | His | Lys | Phe | Asn | Ser | Ser | Arg |
|     |     |     | 100 |     |     |     |     | 105 |     |     |     |     | 110 |     |     |
| Ala | Glu | Ser | Val | Leu | Ala | Ser | Cys | Arg | Phe | Ile | Asp | Glu | Phe | Asp | Gln |
|     |     | 115 |     |     |     |     | 120 |     |     |     |     | 125 |     |     |     |
| Gly | Trp | Gly | Pro | Ile | Thr | Tyr | Thr | Glu | Arg | Asn | Ser | Ser | Asp | Gln | Arg |
|     | 130 |     |     |     |     | 135 |     |     |     |     | 140 |     |     |     |     |
| Pro | Tyr | Cys | Trp | His | Tyr | Pro | Pro | Arg | Gln | Cys | Gly | Ile | Ile | Pro | Ala |
| 145 |     |     |     |     | 150 |     |     |     |     | 155 |     |     |     |     | 160 |
| Ser | Glu | Val | Cys | Gly | Pro | Val | Tyr | Cys | Phe | Thr | Pro | Ser | Pro | Val | Val |
|     |     |     |     | 165 |     |     |     |     | 170 |     |     |     |     | 175 |     |
| Val | Gly | Thr | Thr | Asp | Arg | Phe | Gly | Val | Pro | Thr | Tyr | Ser | Trp | Gly | Glu |
|     |     |     | 180 |     |     |     |     | 185 |     |     |     |     | 190 |     |     |
| Asn | Glu | Thr | Asp | Val | Leu | Val | Leu | Asn | Asn | Thr | Arg | Pro | Pro | Gln | Gly |
|     |     | 195 |     |     |     |     | 200 |     |     |     |     | 205 |     |     |     |
| Asn | Trp | Phe | Gly | Cys | Thr | Trp | Met | Asn | Gly | Thr | Gly | Phe | Thr | Lys | Thr |
|     | 210 |     |     |     |     | 215 |     |     |     |     | 220 |     |     |     |     |
| Cys | Gly | Gly | Pro | Pro | Cys | His | Ile | Gly | Gly | Arg | Gly | Asn | Asn | Thr | Leu |
| 225 |     |     |     |     | 230 |     |     |     |     | 235 |     |     |     |     | 240 |
| Thr | Cys | Pro | Thr | Asp | Cys | Phe | Arg | Lys | His | Pro | Glu | Ala | Thr | Tyr | Thr |
|     |     |     |     | 245 |     |     |     |     | 250 |     |     |     |     | 255 |     |
| Lys | Cys | Gly | Ser | Gly | Pro | Trp | Leu | Thr | Pro | Arg | Cys | Met | Val | Asp | Tyr |
|     |     |     | 260 |     |     |     |     | 265 |     |     |     |     | 270 |     |     |
| Pro | Tyr | Arg | Leu | Trp | His | Tyr | Pro | Cys | Thr | Val | Asn | Phe | Thr | Thr | Phe |
|     |     | 275 |     |     |     |     | 280 |     |     |     |     | 285 |     |     |     |

| | | | | | | | | | | | | | | |
|---|---|---|---|---|---|---|---|---|---|---|---|---|---|---|
| Lys | Val | Arg | Met | Tyr | Val | Gly | Gly | Val | Glu | His | Arg | Leu | Ile | Ala | Ala |
| | 290 | | | | 295 | | | | | 300 | | | | | |
| Cys | Asn | Trp | Thr | Arg | Gly | Asp | Arg | Cys | Asn | Leu | Glu | Asp | Arg | Asp | Arg |
| 305 | | | | | 310 | | | | | 315 | | | | | 320 |
| Ser | Glu | Leu | Ser | Pro | Leu | Leu | Leu | Ser | Thr | Thr | Glu | Trp | Gln | Ile | Leu |
| | | | | 325 | | | | | 330 | | | | | 335 | |
| Pro | Cys | Ser | Phe | Thr | Thr | Leu | Pro | Ala | Leu | Ser | Thr | Gly | Leu | Ile | His |
| | | | 340 | | | | | 345 | | | | | 350 | | |
| Leu | His | Gln | Asn | Ile | Val | Asp | Val | Gln | Tyr | Leu | Tyr | Gly | Ile | Gly | Ser |
| | | 355 | | | | 360 | | | | | | 365 | | | |
| Ala | Val | Val | Ser | Ile | Ala | Ile | Arg | Trp | Glu | Tyr | Val | Leu | Leu | Leu | Phe |
| | 370 | | | | | 375 | | | | | 380 | | | | |
| Leu | Leu | Leu | Ala | Asp | Ala | Arg | Val | Cys | Ala | Cys | Leu | Trp | Met | Met | Leu |
| 385 | | | | | 390 | | | | | 395 | | | | | 400 |
| Leu | Ile |

( 2 ) INFORMATION FOR SEQ ID NO:12:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Hepatitis C virus ( v i i ) IMMEDIATE SOURCE:
        ( B ) CLONE: HCV1

( i x ) FEATURE:
        ( A ) NAME/KEY: CDS
        ( B ) LOCATION: 2..1207

( x i ) SEQUENCE DESCRIPTION: SEQ ID NO:12:

```
G ATC CCA CAA GCC ATC TTG GAC ATG ATC GCT GGT GCT CAC TGG GGA        46
  Ile Pro Gln Ala Ile Leu Asp Met Ile Ala Gly Ala His Trp Gly
    1               5                  10                  15

GTC CTG GCG GGC ATA GCG TAT TTC TCC ATG GTG GGG AAC TGG GCG AAG      94
Val Leu Ala Gly Ile Ala Tyr Phe Ser Met Val Gly Asn Trp Ala Lys
                 20                  25                  30

GTC CTG GTA GTG CTG CTG CTA TTT GCC GGC GTC GAC GCG GAA ACC CAC     142
Val Leu Val Val Leu Leu Leu Phe Ala Gly Val Asp Ala Glu Thr His
             35                  40                  45

GTC ACC GGG GGA AGT GCC GGC CAC ACT GTG TCT GGA TTT GTT AGC CTC     190
Val Thr Gly Gly Ser Ala Gly His Thr Val Ser Gly Phe Val Ser Leu
         50                  55                  60

CTC GCA CCA GGC GCC AAG CAG AAC GTC CAG CTG ATC AAC ACC AAC GGC     238
Leu Ala Pro Gly Ala Lys Gln Asn Val Gln Leu Ile Asn Thr Asn Gly
     65                  70                  75

AGT TGG CAC CTC AAT AGC ACG GCC CTG AAC TGC AAT GAT AGC CTC AAC     286
Ser Trp His Leu Asn Ser Thr Ala Leu Asn Cys Asn Asp Ser Leu Asn
 80                  85                  90                  95

ACC GGC TGG TTG GCA GGG CTT TTC TAT CAC CAC AAG TTC AAC TCT TCA     334
Thr Gly Trp Leu Ala Gly Leu Phe Tyr His His Lys Phe Asn Ser Ser
                100                 105                 110

GGC TGT CCT GAG AGG CTA GCC AGC TGC CGA CCC CTT ACC GAT TTT GAC     382
Gly Cys Pro Glu Arg Leu Ala Ser Cys Arg Pro Leu Thr Asp Phe Asp
            115                 120                 125
```

| | | | | | | | | | | | | | | | | |
|---|---|---|---|---|---|---|---|---|---|---|---|---|---|---|---|---|
| CAG | GGC | TGG | GGC | CCT | ATC | AGT | TAT | GCC | AAC | GGA | AGC | GGC | CCC | GAC | CAG | 430 |
| Gln | Gly | Trp | Gly | Pro | Ile | Ser | Tyr | Ala | Asn | Gly | Ser | Gly | Pro | Asp | Gln | |
| | | 130 | | | | 135 | | | | | 140 | | | | | |
| CGC | CCC | TAC | TGC | TGG | CAC | TAC | CCC | CCA | AAA | CCT | TGC | GGT | ATT | GTG | CCC | 478 |
| Arg | Pro | Tyr | Cys | Trp | His | Tyr | Pro | Pro | Lys | Pro | Cys | Gly | Ile | Val | Pro | |
| | 145 | | | | | 150 | | | | | 155 | | | | | |
| GCG | AAG | AGT | GTG | TGT | GGT | CCG | GTA | TAT | TGC | TTC | ACT | CCC | AGC | CCC | GTG | 526 |
| Ala | Lys | Ser | Val | Cys | Gly | Pro | Val | Tyr | Cys | Phe | Thr | Pro | Ser | Pro | Val | |
| 160 | | | | | 165 | | | | | 170 | | | | | 175 | |
| GTG | GTG | GGA | ACG | ACC | GAC | AGG | TCG | GGC | GCG | CCC | ACC | TAC | AGC | TGG | GGT | 574 |
| Val | Val | Gly | Thr | Thr | Asp | Arg | Ser | Gly | Ala | Pro | Thr | Tyr | Ser | Trp | Gly | |
| | | | | 180 | | | | | 185 | | | | | 190 | | |
| GAA | AAT | GAT | ACG | GAC | GTC | TTC | GTC | CTT | AAC | AAT | ACC | AGG | CCA | CCG | CTG | 622 |
| Glu | Asn | Asp | Thr | Asp | Val | Phe | Val | Leu | Asn | Asn | Thr | Arg | Pro | Pro | Leu | |
| | | | | 195 | | | | | 200 | | | | | 205 | | |
| GGC | AAT | TGG | TTC | GGT | TGT | ACC | TGG | ATG | AAC | TCA | ACT | GGA | TTC | ACC | AAA | 670 |
| Gly | Asn | Trp | Phe | Gly | Cys | Thr | Trp | Met | Asn | Ser | Thr | Gly | Phe | Thr | Lys | |
| | | 210 | | | | | 215 | | | | | 220 | | | | |
| GTG | TGC | GGA | GCG | CCT | CCT | TGT | GTC | ATC | GGA | GGG | GCG | GGC | AAC | AAC | ACC | 718 |
| Val | Cys | Gly | Ala | Pro | Pro | Cys | Val | Ile | Gly | Gly | Ala | Gly | Asn | Asn | Thr | |
| | 225 | | | | | 230 | | | | | 235 | | | | | |
| CTG | CAC | TGC | CCC | ACT | GAT | TGC | TTC | CGC | AAG | CAT | CCG | GAC | GCC | ACA | TAC | 766 |
| Leu | His | Cys | Pro | Thr | Asp | Cys | Phe | Arg | Lys | His | Pro | Asp | Ala | Thr | Tyr | |
| 240 | | | | | 245 | | | | | 250 | | | | | 255 | |
| TCT | CGG | TGC | GGC | TCC | GGT | CCC | TGG | ATC | ACA | CCC | AGG | TGC | CTG | GTC | GAC | 814 |
| Ser | Arg | Cys | Gly | Ser | Gly | Pro | Trp | Ile | Thr | Pro | Arg | Cys | Leu | Val | Asp | |
| | | | | 260 | | | | | 265 | | | | | 270 | | |
| TAC | CCG | TAT | AGG | CTT | TGG | CAT | TAT | CCT | TGT | ACC | ATC | AAC | TAC | ACC | ATA | 862 |
| Tyr | Pro | Tyr | Arg | Leu | Trp | His | Tyr | Pro | Cys | Thr | Ile | Asn | Tyr | Thr | Ile | |
| | | | 275 | | | | | 280 | | | | | 285 | | | |
| TTT | AAA | ATC | AGG | ATG | TAC | GTG | GGA | GGG | GTC | GAA | CAC | AGG | CTG | GAA | GCT | 910 |
| Phe | Lys | Ile | Arg | Met | Tyr | Val | Gly | Gly | Val | Glu | His | Arg | Leu | Glu | Ala | |
| | | | 290 | | | | | 295 | | | | | 300 | | | |
| GCC | TGC | AAC | TGG | ACG | CGG | GGC | GAA | CGT | TGC | GAT | CTG | GAA | GAC | AGG | GAC | 958 |
| Ala | Cys | Asn | Trp | Thr | Arg | Gly | Glu | Arg | Cys | Asp | Leu | Glu | Asp | Arg | Asp | |
| | 305 | | | | | 310 | | | | | 315 | | | | | |
| AGG | TCC | GAG | CTC | AGC | CCG | TTA | CTG | CTG | ACC | ACT | ACA | CAG | TGG | CAG | GTC | 1006 |
| Arg | Ser | Glu | Leu | Ser | Pro | Leu | Leu | Leu | Thr | Thr | Thr | Gln | Trp | Gln | Val | |
| 320 | | | | | 325 | | | | | 330 | | | | | 335 | |
| CTC | CCG | TGT | TCC | TTC | ACA | ACC | CTA | CCA | GCC | TTG | TCC | ACC | GGC | CTC | ATC | 1054 |
| Leu | Pro | Cys | Ser | Phe | Thr | Thr | Leu | Pro | Ala | Leu | Ser | Thr | Gly | Leu | Ile | |
| | | | | 340 | | | | | 345 | | | | | 350 | | |
| CAC | CTC | CAC | CAG | AAC | ATT | GTG | GAC | GTG | CAG | TAC | TTG | TAC | GGG | GTG | GGG | 1102 |
| His | Leu | His | Gln | Asn | Ile | Val | Asp | Val | Gln | Tyr | Leu | Tyr | Gly | Val | Gly | |
| | | | 355 | | | | | 360 | | | | | 365 | | | |
| TCA | AGC | ATC | GCG | TCC | TGG | GCC | ATT | AAG | TGG | GAG | TAC | GTC | GTT | CTC | CTG | 1150 |
| Ser | Ser | Ile | Ala | Ser | Trp | Ala | Ile | Lys | Trp | Glu | Tyr | Val | Val | Leu | Leu | |
| | | 370 | | | | | 375 | | | | | 380 | | | | |
| TTC | CTT | CTG | CTT | GCA | GAC | GCG | CGC | GTC | TGC | TCC | TGC | TTG | TGG | ATG | ATG | 1198 |
| Phe | Leu | Leu | Leu | Ala | Asp | Ala | Arg | Val | Cys | Ser | Cys | Leu | Trp | Met | Met | |
| | 385 | | | | | 390 | | | | | 395 | | | | | |
| CTA | CTC | ATA | | | | | | | | | | | | | | 1207 |
| Leu | Leu | Ile | | | | | | | | | | | | | | |
| 400 | | | | | | | | | | | | | | | | |

( 2 ) INFORMATION FOR SEQ ID NO:13:

( i ) SEQUENCE CHARACTERISTICS:
    ( A ) LENGTH: 402 amino acids
    ( B ) TYPE: amino acid
    ( D ) TOPOLOGY: linear ( i i ) MOLECULE TYPE: protein ( x i ) SEQUENCE DESCRIPTION: SEQ ID NO:13:

| Ile | Pro | Gln | Ala | Ile | Leu | Asp | Met | Ile | Ala | Gly | Ala | His | Trp | Gly | Val |
|---|---|---|---|---|---|---|---|---|---|---|---|---|---|---|---|
| 1 | | | | 5 | | | | | 10 | | | | | 15 | |
| Leu | Ala | Gly | Ile | Ala | Tyr | Phe | Ser | Met | Val | Gly | Asn | Trp | Ala | Lys | Val |
| | | | 20 | | | | | 25 | | | | | 30 | | |
| Leu | Val | Val | Leu | Leu | Leu | Phe | Ala | Gly | Val | Asp | Ala | Glu | Thr | His | Val |
| | | 35 | | | | | 40 | | | | | 45 | | | |
| Thr | Gly | Gly | Ser | Ala | Gly | His | Thr | Val | Ser | Gly | Phe | Val | Ser | Leu | Leu |
| | 50 | | | | | 55 | | | | | 60 | | | | |
| Ala | Pro | Gly | Ala | Lys | Gln | Asn | Val | Gln | Leu | Ile | Asn | Thr | Asn | Gly | Ser |
| 65 | | | | | 70 | | | | | 75 | | | | | 80 |
| Trp | His | Leu | Asn | Ser | Thr | Ala | Leu | Asn | Cys | Asn | Asp | Ser | Leu | Asn | Thr |
| | | | | 85 | | | | | 90 | | | | | 95 | |
| Gly | Trp | Leu | Ala | Gly | Leu | Phe | Tyr | His | His | Lys | Phe | Asn | Ser | Ser | Gly |
| | | | 100 | | | | | 105 | | | | | 110 | | |
| Cys | Pro | Glu | Arg | Leu | Ala | Ser | Cys | Arg | Pro | Leu | Thr | Asp | Phe | Asp | Gln |
| | | 115 | | | | | 120 | | | | | 125 | | | |
| Gly | Trp | Gly | Pro | Ile | Ser | Tyr | Ala | Asn | Gly | Ser | Gly | Pro | Asp | Gln | Arg |
| | 130 | | | | | 135 | | | | | 140 | | | | |
| Pro | Tyr | Cys | Trp | His | Tyr | Pro | Pro | Lys | Pro | Cys | Gly | Ile | Val | Pro | Ala |
| 145 | | | | | 150 | | | | | 155 | | | | | 160 |
| Lys | Ser | Val | Cys | Gly | Pro | Val | Tyr | Cys | Phe | Thr | Pro | Ser | Pro | Val | Val |
| | | | | 165 | | | | | 170 | | | | | 175 | |
| Val | Gly | Thr | Thr | Asp | Arg | Ser | Gly | Ala | Pro | Thr | Tyr | Ser | Trp | Gly | Glu |
| | | | 180 | | | | | 185 | | | | | 190 | | |
| Asn | Asp | Thr | Asp | Val | Phe | Val | Leu | Asn | Asn | Thr | Arg | Pro | Pro | Leu | Gly |
| | | 195 | | | | | 200 | | | | | 205 | | | |
| Asn | Trp | Phe | Gly | Cys | Thr | Trp | Met | Asn | Ser | Thr | Gly | Phe | Thr | Lys | Val |
| | 210 | | | | | 215 | | | | | 220 | | | | |
| Cys | Gly | Ala | Pro | Pro | Cys | Val | Ile | Gly | Gly | Ala | Gly | Asn | Asn | Thr | Leu |
| 225 | | | | | 230 | | | | | 235 | | | | | 240 |
| His | Cys | Pro | Thr | Asp | Cys | Phe | Arg | Lys | His | Pro | Asp | Ala | Thr | Tyr | Ser |
| | | | | 245 | | | | | 250 | | | | | 255 | |
| Arg | Cys | Gly | Ser | Gly | Pro | Trp | Ile | Thr | Pro | Arg | Cys | Leu | Val | Asp | Tyr |
| | | | 260 | | | | | 265 | | | | | 270 | | |
| Pro | Tyr | Arg | Leu | Trp | His | Tyr | Pro | Cys | Thr | Ile | Asn | Tyr | Thr | Ile | Phe |
| | | 275 | | | | | 280 | | | | | 285 | | | |
| Lys | Ile | Arg | Met | Tyr | Val | Gly | Gly | Val | Glu | His | Arg | Leu | Glu | Ala | Ala |
| | 290 | | | | | 295 | | | | | 300 | | | | |
| Cys | Asn | Trp | Thr | Arg | Gly | Glu | Arg | Cys | Asp | Leu | Glu | Asp | Arg | Asp | Arg |
| 305 | | | | | 310 | | | | | 315 | | | | | 320 |
| Ser | Glu | Leu | Ser | Pro | Leu | Leu | Leu | Thr | Thr | Thr | Gln | Trp | Gln | Val | Leu |
| | | | | 325 | | | | | 330 | | | | | 335 | |
| Pro | Cys | Ser | Phe | Thr | Thr | Leu | Pro | Ala | Leu | Ser | Thr | Gly | Leu | Ile | His |
| | | | 340 | | | | | 345 | | | | | 350 | | |
| Leu | His | Gln | Asn | Ile | Val | Asp | Val | Gln | Tyr | Leu | Tyr | Gly | Val | Gly | Ser |
| | | 355 | | | | | 360 | | | | | 365 | | | |
| Ser | Ile | Ala | Ser | Trp | Ala | Ile | Lys | Trp | Glu | Tyr | Val | Val | Leu | Leu | Phe |
| | 370 | | | | | 375 | | | | | 380 | | | | |
| Leu | Leu | Leu | Ala | Asp | Ala | Arg | Val | Cys | Ser | Cys | Leu | Trp | Met | Met | Leu |
| 385 | | | | | 390 | | | | | 395 | | | | | 400 |

Leu Ile ( 2 ) INFORMATION FOR SEQ ID NO:14:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Hepatitis C virus ( v i i ) IMMEDIATE SOURCE:
        ( B ) CLONE: H77

( i x ) FEATURE:
        ( A ) NAME/KEY: CDS
        ( B ) LOCATION: 2..1207

( x i ) SEQUENCE DESCRIPTION: SEQ ID NO:14:

```
G ATC CCA CAA GCC ATC ATG GAC ATG ATC GCT GGT GCT CAC TGG GGA          46
  Ile Pro Gln Ala Ile Met Asp Met Ile Ala Gly Ala His Trp Gly
   1           5                  10                  15

GTC CTG GCG GGC ATA GCG TAT TTC TCC ATG GTG GGG AAC TGG GCG AAG        94
Val Leu Ala Gly Ile Ala Tyr Phe Ser Met Val Gly Asn Trp Ala Lys
             20                  25                  30

GTC CTG GTA GTG CTG CTG CTA TTT GCC GGC GTC GAC GCG GAA ACC CAC       142
Val Leu Val Val Leu Leu Leu Phe Ala Gly Val Asp Ala Glu Thr His
             35                  40                  45

GTC ACC GGG GGA AGT GCC GGC CGC ACC ACG GCT GGG CTT GTT GGT CTC       190
Val Thr Gly Gly Ser Ala Gly Arg Thr Thr Ala Gly Leu Val Gly Leu
         50                  55                  60

CTT ACA CCA GGC GCC AAG CAG AAC ATC CAA CTG ATC AAC ACC AAC GGC       238
Leu Thr Pro Gly Ala Lys Gln Asn Ile Gln Leu Ile Asn Thr Asn Gly
         65                  70                  75

AGT GGC TGG TTA GCA GGG CTC TTC TAT CAC CAC AAA TTC AAC TCT TCA       286
Ser Gly Trp Leu Ala Gly Leu Phe Tyr His His Lys Phe Asn Ser Ser
 80                  85                  90                  95

GGC TGT CCT GAG AGG TTG GCC AGC TGC CGA CGC CTT ACC GAT TTT GCC       334
Gly Cys Pro Glu Arg Leu Ala Ser Cys Arg Arg Leu Thr Asp Phe Ala
                 100                 105                 110

CAG TGG CAC ATC AAT AGC ACG GCC TTG AAC TGC AAT GAA AGC CTT AAC       382
Gln Trp His Ile Asn Ser Thr Ala Leu Asn Cys Asn Glu Ser Leu Asn
             115                 120                 125

ACC GGC TGG GGT CCT ATC AGT TAT GCC AAC GGA AGC GGC CTC GAC GAA       430
Thr Gly Trp Gly Pro Ile Ser Tyr Ala Asn Gly Ser Gly Leu Asp Glu
         130                 135                 140

CGC CCC TAC TGC TGG CAC TAC CCT CCA AGA CCT TGT GGC ATT GTG CCC       478
Arg Pro Tyr Cys Trp His Tyr Pro Pro Arg Pro Cys Gly Ile Val Pro
     145                 150                 155

GCA AAG AGC GTG TGT GGC CCG GTA TAT TGC TTC ACT CCC AGC CCC GTG       526
Ala Lys Ser Val Cys Gly Pro Val Tyr Cys Phe Thr Pro Ser Pro Val
160                 165                 170                 175

GTG GTG GGA ACG ACC GAC AGG TCG GGC GCG CCT ACC TAC AGC TGG GGT       574
Val Val Gly Thr Thr Asp Arg Ser Gly Ala Pro Thr Tyr Ser Trp Gly
                 180                 185                 190

GCA AAT GAT ACG GAT GTC TTC GTC CTT AAC AAC ACC AGG CCA CCG CTG       622
Ala Asn Asp Thr Asp Val Phe Val Leu Asn Asn Thr Arg Pro Pro Leu
             195                 200                 205

GGC AAT TGG TTC GGT TGT ACC TGG ATG AAC TCA ACT GGA TTC ACC AAA       670
```

-continued

```
        Gly Asn Trp Phe Gly Cys Thr Trp Met Asn Ser Thr Gly Phe Thr Lys
                210                 215                 220

GTG TGC GGA GCG CCC CCT TGT GTC ATC GGA GGG GTG GGC AAC AAC ACC        718
Val Cys Gly Ala Pro Pro Cys Val Ile Gly Gly Val Gly Asn Asn Thr
    225                 230                 235

TTG CTC TGC CCC ACT GAT TGC TTC CGC AAG CAT CCG GAA GCC ACA TAC        766
Leu Leu Cys Pro Thr Asp Cys Phe Arg Lys His Pro Glu Ala Thr Tyr
240                 245                 250                 255

TCT CGG TGC GGC TCC GGT CCC TGG ATT ACA CCC AGG TGC ATG GTC GAC        814
Ser Arg Cys Gly Ser Gly Pro Trp Ile Thr Pro Arg Cys Met Val Asp
                260                 265                 270

TAC CCG TAT AGG CTT TGG CAC TAT CCT TGT ACC ATC AAT TAC ACC ATA        862
Tyr Pro Tyr Arg Leu Trp His Tyr Pro Cys Thr Ile Asn Tyr Thr Ile
                275                 280                 285

TTC AAA GTC AGG ATG TAC GTG GGA GGG GTC GAG CAC AGG CTG GAA GCG        910
Phe Lys Val Arg Met Tyr Val Gly Gly Val Glu His Arg Leu Glu Ala
                290                 295                 300

GCC TGC AAC TGG ACG CGG GGC GAA CGC TGT GAT CTG GAA GAC AGG GAC        958
Ala Cys Asn Trp Thr Arg Gly Glu Arg Cys Asp Leu Glu Asp Arg Asp
    305                 310                 315

AGG TCC GAG CTC AGC CCA TTG CTG CTG TCC ACC ACA CAG TGG CAG GTC       1006
Arg Ser Glu Leu Ser Pro Leu Leu Leu Ser Thr Thr Gln Trp Gln Val
320                 325                 330                 335

CTT CCG TGT TCT TTC ACG ACC CTG CCA GCC TTG TCC ACC GGC CTC ATC       1054
Leu Pro Cys Ser Phe Thr Thr Leu Pro Ala Leu Ser Thr Gly Leu Ile
                340                 345                 350

CAC CTC CAC CAG AAC ATT GTG GAC GTG CAG TAC TTG TAC GGG GTA GGG       1102
His Leu His Gln Asn Ile Val Asp Val Gln Tyr Leu Tyr Gly Val Gly
                355                 360                 365

TCA AGC ATC GCG TCC TGG GCC ATT AAG TGG GAG TAC GTC GTT CTC CTG       1150
Ser Ser Ile Ala Ser Trp Ala Ile Lys Trp Glu Tyr Val Val Leu Leu
                370                 375                 380

TTC CTT CTG CTT GCA GAC GCG CGC GTC TGC TCC TGC TTG TGG ATG ATG       1198
Phe Leu Leu Leu Ala Asp Ala Arg Val Cys Ser Cys Leu Trp Met Met
385                 390                 395

TTA CTC ATA                                                          1207
Leu Leu Ile
400
```

( 2 ) INFORMATION FOR SEQ ID NO:15:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Ile Pro Gln Ala Ile Met Asp Met Ile Ala Gly Ala His Trp Gly Val
 1               5                  10                  15

Leu Ala Gly Ile Ala Tyr Phe Ser Met Val Gly Asn Trp Ala Lys Val
                20                  25                  30

Leu Val Val Leu Leu Leu Phe Ala Gly Val Asp Ala Glu Thr His Val
            35                  40                  45

Thr Gly Gly Ser Ala Gly Arg Thr Thr Ala Gly Leu Val Gly Leu Leu
    50                  55                  60

Thr Pro Gly Ala Lys Gln Asn Ile Gln Leu Ile Asn Thr Asn Gly Ser
65                  70                  75                  80

Gly Trp Leu Ala Gly Leu Phe Tyr His His Lys Phe Asn Ser Ser Gly
                85                  90                  95
```

```
Cys  Pro  Glu  Arg  Leu  Ala  Ser  Cys  Arg  Arg  Leu  Thr  Asp  Phe  Ala  Gln
               100                      105                      110

Trp  His  Ile  Asn  Ser  Thr  Ala  Leu  Asn  Cys  Asn  Glu  Ser  Leu  Asn  Thr
          115                      120                      125

Gly  Trp  Gly  Pro  Ile  Ser  Tyr  Ala  Asn  Gly  Ser  Gly  Leu  Asp  Glu  Arg
     130                      135                      140

Pro  Tyr  Cys  Trp  His  Tyr  Pro  Pro  Arg  Pro  Cys  Gly  Ile  Val  Pro  Ala
145                           150                 155                      160

Lys  Ser  Val  Cys  Gly  Pro  Val  Tyr  Cys  Phe  Thr  Pro  Ser  Pro  Val  Val
                    165                 170                      175

Val  Gly  Thr  Thr  Asp  Arg  Ser  Gly  Ala  Pro  Thr  Tyr  Ser  Trp  Gly  Ala
               180                      185                 190

Asn  Asp  Thr  Asp  Val  Phe  Val  Leu  Asn  Asn  Thr  Arg  Pro  Pro  Leu  Gly
          195                      200                      205

Asn  Trp  Phe  Gly  Cys  Thr  Trp  Met  Asn  Ser  Thr  Gly  Phe  Thr  Lys  Val
     210                      215                      220

Cys  Gly  Ala  Pro  Pro  Cys  Val  Ile  Gly  Gly  Val  Gly  Asn  Asn  Thr  Leu
225                      230                      235                      240

Leu  Cys  Pro  Thr  Asp  Cys  Phe  Arg  Lys  His  Pro  Glu  Ala  Thr  Tyr  Ser
               245                      250                      255

Arg  Cys  Gly  Ser  Gly  Pro  Trp  Ile  Thr  Pro  Arg  Cys  Met  Val  Asp  Tyr
               260                      265                      270

Pro  Tyr  Arg  Leu  Trp  His  Tyr  Pro  Cys  Thr  Ile  Asn  Tyr  Thr  Ile  Phe
          275                      280                      285

Lys  Val  Arg  Met  Tyr  Val  Gly  Gly  Val  Glu  His  Arg  Leu  Glu  Ala  Ala
290                           295                      300

Cys  Asn  Trp  Thr  Arg  Gly  Glu  Arg  Cys  Asp  Leu  Glu  Asp  Arg  Asp  Arg
305                      310                      315                      320

Ser  Glu  Leu  Ser  Pro  Leu  Leu  Leu  Ser  Thr  Thr  Gln  Trp  Gln  Val  Leu
               325                      330                      335

Pro  Cys  Ser  Phe  Thr  Thr  Leu  Pro  Ala  Leu  Ser  Thr  Gly  Leu  Ile  His
               340                      345                      350

Leu  His  Gln  Asn  Ile  Val  Asp  Val  Gln  Tyr  Leu  Tyr  Gly  Val  Gly  Ser
          355                      360                      365

Ser  Ile  Ala  Ser  Trp  Ala  Ile  Lys  Trp  Glu  Tyr  Val  Val  Leu  Leu  Phe
370                      375                      380

Leu  Leu  Leu  Ala  Asp  Ala  Arg  Val  Cys  Ser  Cys  Leu  Trp  Met  Met  Leu
385                      390                      395                      400

Leu  Ile
```

( 2 ) INFORMATION FOR SEQ ID NO:16:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Hepatitis C virus ( v i i ) IMMEDIATE SOURCE:
        ( B ) CLONE: H90

( i x ) FEATURE:

5,747,241

( A ) NAME/KEY: CDS
( B ) LOCATION: 2..1207

( x i ) SEQUENCE DESCRIPTION: SEQ ID NO:16:

```
G ATC CCA CAA GCC ATC ATG GAT ATG ATC GCT GGT GCT CAC TGG GGA              46
  Ile Pro Gln Ala Ile Met Asp Met Ile Ala Gly Ala His Trp Gly
   1               5                  10                  15

GTC CTG GCG GGC ATA GCG TAT TTC TCC ATG GTA GGG AAC TGG GCG AAG            94
Val Leu Ala Gly Ile Ala Tyr Phe Ser Met Val Gly Asn Trp Ala Lys
                 20                  25                  30

GTC CTA GTA GTG CTG CTG CTA TTT GCC GGC GTC GAC GCG GAA ACC CAC           142
Val Leu Val Val Leu Leu Leu Phe Ala Gly Val Asp Ala Glu Thr His
             35                  40                  45

GTC ACC GGG GGA AGT GCC GGC CGC TCC GTG CTT GGG ATT GCT AGT TTC           190
Val Thr Gly Gly Ser Ala Gly Arg Ser Val Leu Gly Ile Ala Ser Phe
         50                  55                  60

CTT ACA CGA GGC CCC AAG CAG AAC ATC CAG CTG ATC AAA ACC AAC GGC           238
Leu Thr Arg Gly Pro Lys Gln Asn Ile Gln Leu Ile Lys Thr Asn Gly
     65                  70                  75

AGT TGG CAC ATC AAT AGC ACG GCC CTG AAC TGC AAT GAC AGC CTT AAC           286
Ser Trp His Ile Asn Ser Thr Ala Leu Asn Cys Asn Asp Ser Leu Asn
 80                  85                  90                  95

GCC GGC TGG ATA GCG GGG CTC TTC TAT CAC CAT GGA TTC AAC TCT TCA           334
Ala Gly Trp Ile Ala Gly Leu Phe Tyr His His Gly Phe Asn Ser Ser
                100                 105                 110

GGC TGT CCT GAG AGG TTG GCC AGC TGC CGA CGC CTT ACC GAT TTT GAC           382
Gly Cys Pro Glu Arg Leu Ala Ser Cys Arg Arg Leu Thr Asp Phe Asp
            115                 120                 125

CAG GGC TGG GGC CCT ATC AGT TAT GCC AAC GGA AGC GGC CCC GAC GAA           430
Gln Gly Trp Gly Pro Ile Ser Tyr Ala Asn Gly Ser Gly Pro Asp Glu
        130                 135                 140

CGT CCC TAC TGC TGG CAC TAC CCC CCA AGA CCT TGT GGC ATT GTG CCC           478
Arg Pro Tyr Cys Trp His Tyr Pro Pro Arg Pro Cys Gly Ile Val Pro
    145                 150                 155

GCA AAG AGC GTG TGT GGC CCG GTA TAC TGC TTC ACT CCC AGC CCC GTG           526
Ala Lys Ser Val Cys Gly Pro Val Tyr Cys Phe Thr Pro Ser Pro Val
160                 165                 170                 175

GTG GTG GGA ACG ACC GAC AGG TCG GGC GCG CCT ACC TAC AAC TGG GGT           574
Val Val Gly Thr Thr Asp Arg Ser Gly Ala Pro Thr Tyr Asn Trp Gly
                180                 185                 190

GAA AAT GAT ACG GAT GTC CTC ATC CTT AAC AAC ACC AGG CCG CCG CTG           622
Glu Asn Asp Thr Asp Val Leu Ile Leu Asn Asn Thr Arg Pro Pro Leu
            195                 200                 205

GGC AAT TGG TTC GGT TGT ACC TGG ATG AAC TCA ACT GGA TTC ACC AAA           670
Gly Asn Trp Phe Gly Cys Thr Trp Met Asn Ser Thr Gly Phe Thr Lys
        210                 215                 220

GTG TGC GGA GCG CCC CCT TGT GTC ATC GGA GGG GTG GGC AAC AAC ACC           718
Val Cys Gly Ala Pro Pro Cys Val Ile Gly Gly Val Gly Asn Asn Thr
    225                 230                 235

TTG CGC TGC CCC ACT GAT TGT TTC CGC AAG CAT CCG GAA GCC ACA TAC           766
Leu Arg Cys Pro Thr Asp Cys Phe Arg Lys His Pro Glu Ala Thr Tyr
240                 245                 250                 255

TCT CGG TGC GGC TCC GGT CCC TGG ATC ACA CCC AGG TGC ATG GTC CAC           814
Ser Arg Cys Gly Ser Gly Pro Trp Ile Thr Pro Arg Cys Met Val His
                260                 265                 270

TAC CCG TAT AGG CTT TGG CAC TAT CCT TGT ACC ATC AAT TAC ACT ATA           862
Tyr Pro Tyr Arg Leu Trp His Tyr Pro Cys Thr Ile Asn Tyr Thr Ile
            275                 280                 285

TTT AAA GTC AGG ATG TAC GTG GGA GGG ATC GAG CAC AGG CTG GAA GCG           910
Phe Lys Val Arg Met Tyr Val Gly Gly Ile Glu His Arg Leu Glu Ala
        290                 295                 300
```

-continued

| | | | | | | | | | | | | | | | | |
|---|---|---|---|---|---|---|---|---|---|---|---|---|---|---|---|---|
| GCC | TGC | AAC | TGG | ACG | CGG | GGC | GAA | CGT | TGC | GAT | CTG | GAA | GAC | AGG | GAC | 958 |
| Ala | Cys | Asn | Trp | Thr | Arg | Gly | Glu | Arg | Cys | Asp | Leu | Glu | Asp | Arg | Asp | |
| | 305 | | | | 310 | | | | | | 315 | | | | | |
| AGG | TCC | GAG | CTC | AGC | CCA | TTG | CTG | CTG | TCC | ACT | ACG | CAG | TGG | CAG | GTC | 1006 |
| Arg | Ser | Glu | Leu | Ser | Pro | Leu | Leu | Leu | Ser | Thr | Thr | Gln | Trp | Gln | Val | |
| 320 | | | | | 325 | | | | | 330 | | | | | 335 | |
| CTT | CCG | TGT | TCT | TTC | ACG | ACC | CTG | CCA | GCC | TTG | TCC | ACC | GGC | CTC | ATC | 1054 |
| Leu | Pro | Cys | Ser | Phe | Thr | Thr | Leu | Pro | Ala | Leu | Ser | Thr | Gly | Leu | Ile | |
| | | | | 340 | | | | | 345 | | | | | 350 | | |
| CAC | CTC | CAC | CAG | AAC | ATT | GTG | GAC | GTG | CAG | TAC | TTG | TAC | GGG | GTA | GGG | 1102 |
| His | Leu | His | Gln | Asn | Ile | Val | Asp | Val | Gln | Tyr | Leu | Tyr | Gly | Val | Gly | |
| | | | 355 | | | | 360 | | | | | | 365 | | | |
| TCA | AGC | ATC | GCG | TCC | TGG | ACC | ATC | AAG | TGG | GAG | TAC | GTC | GTT | CTC | CTG | 1150 |
| Ser | Ser | Ile | Ala | Ser | Trp | Thr | Ile | Lys | Trp | Glu | Tyr | Val | Val | Leu | Leu | |
| | | 370 | | | | | 375 | | | | | 380 | | | | |
| TTC | CTC | CTG | CTT | GCA | GAC | GCG | CGC | GTC | TGC | TCC | TGC | TTG | TGG | ATG | ATG | 1198 |
| Phe | Leu | Leu | Leu | Ala | Asp | Ala | Arg | Val | Cys | Ser | Cys | Leu | Trp | Met | Met | |
| | 385 | | | | | 390 | | | | | 395 | | | | | |
| TTA | CTC | ATA | | | | | | | | | | | | | | 1207 |
| Leu | Leu | Ile | | | | | | | | | | | | | | |
| 400 | | | | | | | | | | | | | | | | |

( 2 ) INFORMATION FOR SEQ ID NO:17:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | |
|---|---|---|---|---|---|---|---|---|---|---|---|---|---|---|
| Ile | Pro | Gln | Ala | Ile | Met | Asp | Met | Ile | Ala | Gly | Ala | His | Trp | Gly | Val |
| 1 | | | | 5 | | | | | 10 | | | | | 15 | |
| Leu | Ala | Gly | Ile | Ala | Tyr | Phe | Ser | Met | Val | Gly | Asn | Trp | Ala | Lys | Val |
| | | | | 20 | | | | 25 | | | | | 30 | | |
| Leu | Val | Val | Leu | Leu | Leu | Phe | Ala | Gly | Val | Asp | Ala | Glu | Thr | His | Val |
| | | | 35 | | | | | 40 | | | | | 45 | | |
| Thr | Gly | Gly | Ser | Ala | Gly | Arg | Ser | Val | Leu | Gly | Ile | Ala | Ser | Phe | Leu |
| | 50 | | | | | 55 | | | | | 60 | | | | |
| Thr | Arg | Gly | Pro | Lys | Gln | Asn | Ile | Gln | Leu | Ile | Lys | Thr | Asn | Gly | Ser |
| 65 | | | | | 70 | | | | | 75 | | | | | 80 |
| Trp | His | Ile | Asn | Ser | Thr | Ala | Leu | Asn | Cys | Asn | Asp | Ser | Leu | Asn | Ala |
| | | | | 85 | | | | | 90 | | | | | 95 | |
| Gly | Trp | Ile | Ala | Gly | Leu | Phe | Tyr | His | His | Gly | Phe | Asn | Ser | Ser | Gly |
| | | | 100 | | | | | 105 | | | | | 110 | | |
| Cys | Pro | Glu | Arg | Leu | Ala | Ser | Cys | Arg | Arg | Leu | Thr | Asp | Phe | Asp | Gln |
| | | | 115 | | | | | 120 | | | | | 125 | | |
| Gly | Trp | Gly | Pro | Ile | Ser | Tyr | Ala | Asn | Gly | Ser | Gly | Pro | Asp | Glu | Arg |
| | | 130 | | | | | 135 | | | | | 140 | | | |
| Pro | Tyr | Cys | Trp | His | Tyr | Pro | Pro | Arg | Pro | Cys | Gly | Ile | Val | Pro | Ala |
| 145 | | | | | 150 | | | | | 155 | | | | | 160 |
| Lys | Ser | Val | Cys | Gly | Pro | Val | Tyr | Cys | Phe | Thr | Pro | Ser | Pro | Val | Val |
| | | | | 165 | | | | | 170 | | | | | 175 | |
| Val | Gly | Thr | Thr | Asp | Arg | Ser | Gly | Ala | Pro | Thr | Tyr | Asn | Trp | Gly | Glu |
| | | | | 180 | | | | | 185 | | | | | 190 | |
| Asn | Asp | Thr | Asp | Val | Leu | Ile | Leu | Asn | Asn | Thr | Arg | Pro | Pro | Leu | Gly |
| | | | 195 | | | | | 200 | | | | | 205 | | |

| Asn | Trp | Phe | Gly | Cys | Thr | Trp | Met | Asn | Ser | Thr | Gly | Phe | Thr | Lys | Val |
| | | | | 210 | | | | 215 | | | | 220 | | | |
| Cys | Gly | Ala | Pro | Pro | Cys | Val | Ile | Gly | Gly | Val | Gly | Asn | Asn | Thr | Leu |
| 225 | | | | | 230 | | | | 235 | | | | | | 240 |
| Arg | Cys | Pro | Thr | Asp | Cys | Phe | Arg | Lys | His | Pro | Glu | Ala | Thr | Tyr | Ser |
| | | | | 245 | | | | | 250 | | | | | 255 | |
| Arg | Cys | Gly | Ser | Gly | Pro | Trp | Ile | Thr | Pro | Arg | Cys | Met | Val | His | Tyr |
| | | | | 260 | | | | 265 | | | | | 270 | | |
| Pro | Tyr | Arg | Leu | Trp | His | Tyr | Pro | Cys | Thr | Ile | Asn | Tyr | Thr | Ile | Phe |
| | | | 275 | | | | | 280 | | | | 285 | | | |
| Lys | Val | Arg | Met | Tyr | Val | Gly | Gly | Ile | Glu | His | Arg | Leu | Glu | Ala | Ala |
| | | 290 | | | | | 295 | | | | | 300 | | | |
| Cys | Asn | Trp | Thr | Arg | Gly | Glu | Arg | Cys | Asp | Leu | Glu | Asp | Arg | Asp | Arg |
| 305 | | | | | 310 | | | | | 315 | | | | | 320 |
| Ser | Glu | Leu | Ser | Pro | Leu | Leu | Leu | Ser | Thr | Thr | Gln | Trp | Gln | Val | Leu |
| | | | | 325 | | | | | 330 | | | | | 335 | |
| Pro | Cys | Ser | Phe | Thr | Thr | Leu | Pro | Ala | Leu | Ser | Thr | Gly | Leu | Ile | His |
| | | | 340 | | | | | 345 | | | | | 350 | | |
| Leu | His | Gln | Asn | Ile | Val | Asp | Val | Gln | Tyr | Leu | Tyr | Gly | Val | Gly | Ser |
| | | | 355 | | | | | 360 | | | | | 365 | | |
| Ser | Ile | Ala | Ser | Trp | Thr | Ile | Lys | Trp | Glu | Tyr | Val | Val | Leu | Leu | Phe |
| | 370 | | | | | 375 | | | | | 380 | | | | |
| Leu | Leu | Leu | Ala | Asp | Ala | Arg | Val | Cys | Ser | Cys | Leu | Trp | Met | Met | Leu |
| 385 | | | | | 390 | | | | | 395 | | | | | 400 |
| Leu | Ile | | | | | | | | | | | | | | |

( 2 ) INFORMATION FOR SEQ ID NO:18:

( i ) SEQUENCE CHARACTERISTICS:
        ( A ) LENGTH: 523 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Hepatitis C virus ( v i i ) IMMEDIATE SOURCE:
        ( B ) CLONE: J1(JM)

( i x ) FEATURE:
        ( A ) NAME/KEY: CDS
        ( B ) LOCATION: 2..523

( x i ) SEQUENCE DESCRIPTION: SEQ ID NO:18:

| G | ATC | CCA | CAA | GCC | ATC | TTG | GAT | ATG | ATC | GCT | GGT | GCT | CAC | TGG | GGA | | 46 |
| | Ile | Pro | Gln | Ala | Ile | Leu | Asp | Met | Ile | Ala | Gly | Ala | His | Trp | Gly | | |
| | 1 | | | | 5 | | | | | 10 | | | | | 15 | | |
| GTC | CTG | GCG | GGC | ATA | GCG | TAT | TTC | TCC | ATG | GTG | GGG | AAC | TGG | GCG | AAG | | 94 |
| Val | Leu | Ala | Gly | Ile | Ala | Tyr | Phe | Ser | Met | Val | Gly | Asn | Trp | Ala | Lys | | |
| | | | | 20 | | | | | 25 | | | | | 30 | | | |
| GTC | CTG | GTA | GTG | CTG | TTG | CTG | TTT | GCC | GGC | GTC | GAC | GCG | GAA | ACC | ATC | | 142 |
| Val | Leu | Val | Val | Leu | Leu | Leu | Phe | Ala | Gly | Val | Asp | Ala | Glu | Thr | Ile | | |
| | | | | 35 | | | | | 40 | | | | | 45 | | | |
| GTC | TCC | GGG | GGA | CAA | GCC | GCC | CGC | GCC | ATG | TCT | GGA | CTT | GTT | AGT | CTC | | 190 |
| Val | Ser | Gly | Gly | Gln | Ala | Ala | Arg | Ala | Met | Ser | Gly | Leu | Val | Ser | Leu | | |
| | | 50 | | | | | 55 | | | | | 60 | | | | | |
| TTC | ACA | CCA | GGC | GCT | AAG | CAG | AAC | ATC | CAG | CTG | ATC | AAC | ACC | AAC | GGC | | 238 |

```
                    Phe  Thr  Pro  Gly  Ala  Lys  Gln  Asn  Ile  Gln  Leu  Ile  Asn  Thr  Asn  Gly
                         65                       70                      75

AGT  TGG  CAC  ATC  AAT  AGC  ACG  GCC  TTG  AAC  TGC  AAT  GAA  AGC  CTT  AAC                      286
Ser  Trp  His  Ile  Asn  Ser  Thr  Ala  Leu  Asn  Cys  Asn  Glu  Ser  Leu  Asn
80                       85                       90                      95

ACC  GGC  TGG  TTA  GCA  GGG  CTT  ATC  TAT  CAA  CAC  AAA  TTC  AAC  TCT  TCG                      334
Thr  Gly  Trp  Leu  Ala  Gly  Leu  Ile  Tyr  Gln  His  Lys  Phe  Asn  Ser  Ser
                    100                      105                     110

GGC  TGT  CCC  GAG  AGG  TTG  GCC  AGC  TGC  CGA  CGC  CTT  ACC  GAT  TTT  GAC                      382
Gly  Cys  Pro  Glu  Arg  Leu  Ala  Ser  Cys  Arg  Arg  Leu  Thr  Asp  Phe  Asp
               115                      120                     125

CAG  GGC  TGG  GGC  CCT  ATC  AGT  CAT  GCC  AAC  GGA  AGC  GGC  CCC  GAC  CAA                      430
Gln  Gly  Trp  Gly  Pro  Ile  Ser  His  Ala  Asn  Gly  Ser  Gly  Pro  Asp  Gln
          130                      135                     140

CGC  CCC  TAT  TGT  TGG  CAC  TAC  CCC  CCA  AAA  CCT  TGC  GGT  ATC  GTG  CCC                      478
Arg  Pro  Tyr  Cys  Trp  His  Tyr  Pro  Pro  Lys  Pro  Cys  Gly  Ile  Val  Pro
     145                      150                     155

GCA  AAG  AGC  GTA  TGT  GGC  CCG  GTA  TAT  TGC  TTC  ACT  CCC  AGC  CCC                           523
Ala  Lys  Ser  Val  Cys  Gly  Pro  Val  Tyr  Cys  Phe  Thr  Pro  Ser  Pro
160                 165                      170
```

( 2 ) INFORMATION FOR SEQ ID NO:19:

( i ) SEQUENCE CHARACTERISTICS:
        ( A ) LENGTH: 174 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Ile  Pro  Gln  Ala  Ile  Leu  Asp  Met  Ile  Ala  Gly  Ala  His  Trp  Gly  Val
1                   5                        10                      15

Leu  Ala  Gly  Ile  Ala  Tyr  Phe  Ser  Met  Val  Gly  Asn  Trp  Ala  Lys  Val
                    20                       25                      30

Leu  Val  Val  Leu  Leu  Leu  Phe  Ala  Gly  Val  Asp  Ala  Glu  Thr  Ile  Val
                    35                       40                      45

Ser  Gly  Gly  Gln  Ala  Ala  Arg  Ala  Met  Ser  Gly  Leu  Val  Ser  Leu  Phe
          50                       55                       60

Thr  Pro  Gly  Ala  Lys  Gln  Asn  Ile  Gln  Leu  Ile  Asn  Thr  Asn  Gly  Ser
65                       70                       75                      80

Trp  His  Ile  Asn  Ser  Thr  Ala  Leu  Asn  Cys  Asn  Glu  Ser  Leu  Asn  Thr
                    85                       90                      95

Gly  Trp  Leu  Ala  Gly  Leu  Ile  Tyr  Gln  His  Lys  Phe  Asn  Ser  Ser  Gly
                    100                      105                     110

Cys  Pro  Glu  Arg  Leu  Ala  Ser  Cys  Arg  Arg  Leu  Thr  Asp  Phe  Asp  Gln
               115                      120                     125

Gly  Trp  Gly  Pro  Ile  Ser  His  Ala  Asn  Gly  Ser  Gly  Pro  Asp  Gln  Arg
          130                      135                     140

Pro  Tyr  Cys  Trp  His  Tyr  Pro  Pro  Lys  Pro  Cys  Gly  Ile  Val  Pro  Ala
145                      150                      155                     160

Lys  Ser  Val  Cys  Gly  Pro  Val  Tyr  Cys  Phe  Thr  Pro  Ser  Pro
                    165                      170
```

( 2 ) INFORMATION FOR SEQ ID NO:20:

( i ) SEQUENCE CHARACTERISTICS:
        ( A ) LENGTH: 523 base pairs
        ( B ) TYPE: nucleic acid
        ( C ) STRANDEDNESS: double
        ( D ) TOPOLOGY: linear (  i i  ) MOLECULE TYPE: DNA (genomic)

(  i v  ) ANTI-SENSE: NO (  v i  ) ORIGINAL SOURCE:
  ( A ) ORGANISM: Hepatitis C virus (  v i i  ) IMMEDIATE SOURCE:
  ( B ) CLONE: J4(JM)

(  i x  ) FEATURE:
  ( A ) NAME/KEY: CDS
  ( B ) LOCATION: 2..523

(  x i  ) SEQUENCE DESCRIPTION: SEQ ID NO:20:

```
G ATC CCA CAA GCT GTC GTG GAC ATG GTG GCG GGG GCC CAC TGG GGA        46
  Ile Pro Gln Ala Val Val Asp Met Val Ala Gly Ala His Trp Gly
  1               5                   10                  15

GTC CTG GCG GGC CTT GCC TAC TAT TCC ATG GTA GGG AAC TGG GCT AAG      94
Val Leu Ala Gly Leu Ala Tyr Tyr Ser Met Val Gly Asn Trp Ala Lys
                20                  25                  30

GTC CTG ATT GTG GCG CTA CTC TTC GCC GGC GTT GAC GGG GAG ACC TAC      142
Val Leu Ile Val Ala Leu Leu Phe Ala Gly Val Asp Gly Glu Thr Tyr
            35                  40                  45

ACG TCG GGG GGG GCG GCC AGC CAC ACC ACC TCC ACG CTC GCG TCC CTC      190
Thr Ser Gly Gly Ala Ala Ser His Thr Thr Ser Thr Leu Ala Ser Leu
        50                  55                  60

TTC TCA CCT GGG GCG TCT CAG AGA ATC CAG CTT GTG AAT ACC AAC GGC      238
Phe Ser Pro Gly Ala Ser Gln Arg Ile Gln Leu Val Asn Thr Asn Gly
    65                  70                  75

AGC TGG CAC ATC AAC AGG ACT GCC CTA AAC TGC AAT GAC TCC CTC CAC      286
Ser Trp His Ile Asn Arg Thr Ala Leu Asn Cys Asn Asp Ser Leu His
80                  85                  90                  95

ACT GGG TTC CTT GCC GCG CTG TTC TAC ACA CAC AGG TTC AAC TCG TCC      334
Thr Gly Phe Leu Ala Ala Leu Phe Tyr Thr His Arg Phe Asn Ser Ser
                100                 105                 110

GGG TGC CCG GAG CGC ATG GCC AGC TGC CGC CCC ATT GAC TGG TTC GCC      382
Gly Cys Pro Glu Arg Met Ala Ser Cys Arg Pro Ile Asp Trp Phe Ala
            115                 120                 125

CAG GGA TGG GGC CCC ATC ACC TAT ACT GAG CCT GAC AGC CCG GAT CAG      430
Gln Gly Trp Gly Pro Ile Thr Tyr Thr Glu Pro Asp Ser Pro Asp Gln
        130                 135                 140

AGG CCT TAT TGC TGG CAT TAC GCG CCT CGA CCG TGT GGT ATC GTA CCC      478
Arg Pro Tyr Cys Trp His Tyr Ala Pro Arg Pro Cys Gly Ile Val Pro
    145                 150                 155

GCG TCG CAG GTG TGT GGT CCA GTG TAT TGC TTC ACC CCA AGC CCT          523
Ala Ser Gln Val Cys Gly Pro Val Tyr Cys Phe Thr Pro Ser Pro
160                 165                 170
```

( 2 ) INFORMATION FOR SEQ ID NO:21:

(  i  ) SEQUENCE CHARACTERISTICS:
    ( A ) LENGTH: 174 amino acids
    ( B ) TYPE: amino acid
    ( D ) TOPOLOGY: linear (  i i  ) MOLECULE TYPE: protein (  x i  ) SEQUENCE DESCRIPTION: SEQ ID NO:21:

```
Ile Pro Gln Ala Val Val Asp Met Val Ala Gly Ala His Trp Gly Val
1               5                   10                  15

Leu Ala Gly Leu Ala Tyr Tyr Ser Met Val Gly Asn Trp Ala Lys Val
                20                  25                  30

Leu Ile Val Ala Leu Leu Phe Ala Gly Val Asp Gly Glu Thr Tyr Thr
```

-continued

```
                35                        40                         45
Ser  Gly  Gly  Ala  Ala  Ser  His  Thr  Thr  Ser  Thr  Leu  Ala  Ser  Leu  Phe
          50                       55                       60

Ser  Pro  Gly  Ala  Ser  Gln  Arg  Ile  Gln  Leu  Val  Asn  Thr  Asn  Gly  Ser
 65                      70                       75                        80

Trp  His  Ile  Asn  Arg  Thr  Ala  Leu  Asn  Cys  Asn  Asp  Ser  Leu  His  Thr
                    85                       90                       95

Gly  Phe  Leu  Ala  Ala  Leu  Phe  Tyr  Thr  His  Arg  Phe  Asn  Ser  Ser  Gly
               100                      105                      110

Cys  Pro  Glu  Arg  Met  Ala  Ser  Cys  Arg  Pro  Ile  Asp  Trp  Phe  Ala  Gln
               115                      120                      125

Gly  Trp  Gly  Pro  Ile  Thr  Tyr  Thr  Glu  Pro  Asp  Ser  Pro  Asp  Gln  Arg
     130                      135                      140

Pro  Tyr  Cys  Trp  His  Tyr  Ala  Pro  Arg  Pro  Cys  Gly  Ile  Val  Pro  Ala
145                           150                      155                     160

Ser  Gln  Val  Cys  Gly  Pro  Val  Tyr  Cys  Phe  Thr  Pro  Ser  Pro
                    165                      170
```

( 2 ) INFORMATION FOR SEQ ID NO:22:

( i ) SEQUENCE CHARACTERISTICS:
        ( A ) LENGTH: 402 amino acids
        ( B ) TYPE: amino acid
        ( D ) TOPOLOGY: unknown ( i i ) MOLECULE TYPE: protein ( v i ) ORIGINAL SOURCE:
        ( A ) ORGANISM: Hepatitis C virus ( x i ) SEQUENCE DESCRIPTION: SEQ ID NO:22:

```
Ile  Pro  Gln  Ala  Xaa  Xaa  Asp  Met  Xaa  Ala  Gly  Ala  His  Trp  Gly  Val
 1                  5                       10                            15

Leu  Ala  Gly  Xaa  Ala  Tyr  Xaa  Ser  Met  Xaa  Gly  Asn  Trp  Ala  Lys  Val
               20                       25                       30

Leu  Xaa  Val  Xaa  Leu  Leu  Phe  Ala  Gly  Val  Asp  Xaa  Xaa  Thr  Xaa  Xaa
          35                       40                       45

Xaa  Xaa  Xaa  Xaa  Xaa  Xaa  Xaa  Xaa  Xaa  Xaa  Xaa  Xaa  Xaa  Xaa  Xaa  Xaa
     50                       55                       60

Xaa  Xaa  Gly  Xaa  Xaa  Xaa  Xaa  Xaa  Gln  Leu  Xaa  Xaa  Thr  Asn  Gly  Ser
 65                      70                       75                        80

Trp  His  Xaa  Asn  Xaa  Thr  Ala  Leu  Asn  Cys  Asn  Xaa  Ser  Leu  Xaa  Xaa
                    85                       90                       95

Gly  Xaa  Xaa  Ala  Xaa  Leu  Xaa  Tyr  Xaa  His  Xaa  Phe  Xaa  Xaa  Ser  Xaa
               100                      105                      110

Xaa  Xaa  Xaa  Xaa  Xaa  Ala  Xaa  Cys  Xaa  Xaa  Xaa  Xaa  Xaa  Phe  Xaa  Gln
               115                      120                      125

Gly  Trp  Xaa  Pro  Ile  Xaa  Xaa  Xaa  Xaa  Xaa  Xaa  Xaa  Xaa  Xaa  Xaa  Xaa
     130                      135                      140

Pro  Tyr  Cys  Trp  His  Tyr  Xaa  Pro  Xaa  Xaa  Cys  Xaa  Xaa  Val  Pro  Ala
145                           150                      155                     160

Xaa  Xaa  Val  Cys  Gly  Pro  Val  Tyr  Cys  Phe  Thr  Pro  Ser  Pro  Val  Val
                    165                      170                           175

Val  Gly  Thr  Thr  Asp  Arg  Xaa  Gly  Xaa  Pro  Thr  Tyr  Xaa  Trp  Gly  Xaa
               180                      185                      190

Asn  Xaa  Thr  Asp  Val  Xaa  Xaa  Leu  Xaa  Asn  Thr  Arg  Pro  Pro  Xaa  Gly
          195                      200                      205
```

```
    Asn  Trp  Phe  Gly  Cys  Thr  Trp  Met  Asn  Xaa  Thr  Gly  Phe  Thr  Lys  Xaa
         210                      215                      220
    Cys  Gly  Xaa  Pro  Pro  Cys  Xaa  Ile  Xaa  Gly  Xaa  Gly  Asn  Asn  Thr  Leu
    225                      230                      235                      240
    Xaa  Cys  Pro  Thr  Asp  Cys  Phe  Arg  Lys  His  Pro  Xaa  Ala  Thr  Tyr  Xaa
                        245                      250                      255
    Xaa  Cys  Gly  Ser  Gly  Pro  Trp  Xaa  Thr  Pro  Arg  Cys  Xaa  Val  Xaa  Tyr
                   260                      265                      270
    Pro  Tyr  Arg  Leu  Trp  His  Tyr  Pro  Cys  Thr  Xaa  Asn  Xaa  Thr  Xaa  Phe
              275                      280                      285
    Lys  Xaa  Arg  Met  Tyr  Val  Gly  Xaa  Glu  His  Arg  Leu  Xaa  Ala  Ala
         290                      295                      300
    Cys  Asn  Trp  Thr  Arg  Gly  Xaa  Arg  Cys  Xaa  Leu  Glu  Asp  Arg  Asp  Arg
    305                      310                      315                      320
    Xaa  Glu  Leu  Ser  Pro  Leu  Leu  Leu  Xaa  Thr  Thr  Xaa  Trp  Gln  Xaa  Leu
                        325                      330                      335
    Pro  Cys  Ser  Phe  Thr  Thr  Leu  Pro  Ala  Leu  Ser  Thr  Gly  Leu  Ile  His
                   340                      345                      350
    Leu  His  Xaa  Asn  Xaa  Val  Asp  Val  Gln  Tyr  Leu  Tyr  Gly  Xaa  Gly  Ser
              355                      360                      365
    Xaa  Xaa  Xaa  Ser  Xaa  Xaa  Ile  Xaa  Trp  Glu  Tyr  Xaa  Xaa  Leu  Leu  Phe
         370                      375                      380
    Leu  Leu  Leu  Ala  Asp  Ala  Arg  Val  Cys  Xaa  Cys  Leu  Trp  Met  Met  Leu
    385                      390                      395                      400
    Leu  Ile
```

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GCTATCAGCA GCATCATCCA                                                  20

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CAGNTANTCC GGATCCCNCA AG                                             22

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GTAAAACGAC GGCCAGT                                                                   17

(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CAGGAAACAG CTATGAC                                                                   17

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GGACTAGTCC                                                                           10

(2) INFORMATION FOR SEQ ID NO:28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CTAGAGAATT CGGTAC                                                                    16

DIAGNOSTIC REAGENT FOR HEPATITIS C

This is a Division of application Ser. No. 08/325,630, filed on Oct. 19, 1994, pending, which is a continuation of application Ser. No. 07/956,993, filed on Oct. 6, 1992, abandoned.

BACKGROUND OF THE INVENTION

This invention relates to a diagnostic reagent for hepatitis C comprising an antigen protein translated from a genome of hepatitis C virus. More specifically, this invention relates to a diagnostic reagent for detecting an antibody against hepatitis C virus (hereinafter referred to as "HCV"), which comprises a protein encoded by a gene of HCV, wherein said protein is identified as a glycoprotein called the second envelope protein or the first non-structural protein (hereinafter referred to as "E2/NS1").

The first successful cloning of human hepatitis virus which had been called non-A, non-B hepatitis virus was accomplished in 1988 by Chiron Co., Ltd. U.S.A and the hepatitis virus was designated HCV. Further, Chiron Co., Ltd. succeeded in expressing in a yeast a fused protein which comprises at the C-terminal the polypeptide corresponding to the region having 363 amino acid residues from the third nonstructural protein (NS3) to the fourth non-structural protein (NS4) both of which are portions of nonstructural proteins of HCV and at the N-terminal human superoxide dismutase(European unexamined patent publication No. 318216) and, using this recombinant antigen, developed a diagnostic reagent for hepatitis C (Science, 244, 359–362, 362–364, (1989)).

In Japan, the Japanese Red Cross Society has been using the diagnostic reagent in the screening of blood provided by donors, which is known as "C100-3 antibody test", in order to avoid post-transfusion hepatitis since the end of 1989. However, since not all samples are effectively screened only by C100-3 antibody test, post-transfusion hepatitis is not completely avoided.

Subsequently, further investigation of HCV genomes derived from the serum of a Japanese patient by the cloning technique revealed that HCV prevailed in Japan is similar to HCV obtained by Chiron Co., Ltd. but a different strain (Protein, Nucleic acid and Enzyme.36, 1679–1691, (1991)). In addition, the use of the core protein (C) region of the structural protein, the third non-structural protein (NS3) region, the fifth non-structural protein region and the like have been proposed as more effective diagnostic reagents than C100–3 (Lancet, 337, 317–319, 1991 and Japanese unexamined patent publication (hereinafter referred to as "J. P. KOKAI") No. Hei 3-103180).

The C100-3 antibody test system has a disadvantage that the detection rate and the sensitivity are low as mentioned above. Although proteins derived from C, NS3 and NS5 regions have been proposed as more effective antigens for detection than C100-3, any satisfactory results have not yet been reported. Therefore, there is a need for a diagnostic reagent and a diagnostic method for hepatitis C, having a higher detection rate and sensitivity.

SUMMARY OF THE INVENTION

The inventors have conducted various investigations to obtain a diagnostic reagent for hepatitis C, having a higher detection rate and sensitivity. As a result, they have found that E2/NS1 protein having a sugar chain, which is obtained by expressing cDNA of E2/NS1 region in animal cells reacts with the serum of the patient of hepatitis C with a high rate in a fluorescent antibody test and accomplished the goals of the present invention. The high reaction rate of E2/NS1 region with the serum of the patient of hepatitis C was unexpected because the protein derived from E2/NS1 region is susceptible to the mutation of an amino acid sequence and, therefore, the protein expressed in E. coli has been considered to react with the serum of the patient of hepatitis C with a lower rate comparing with the proteins derived from the other regions of HCV and it has not been expected to use the protein for a diagnostic reagent.

The present invention provides a diagnostic reagent for hepatitis C, which detects an antibody induced by infection of hepatitis C virus, characterised in that said diagnostic reagent comprises the second envelope protein or the first non-structural protein which is encoded by the genome of hepatitis C virus and has a sugar chain.

BRIEF DESCRIPTION OF THE DRAWINGS

FIG. 3 shows the steps of constructing plasmid pSRNot.

FIG. 4 shows the steps of constructing expression vector paSR1325X-3 having a DNA fragment coding for E2/NS1 protein.

DETAILED EXPLANATION OF THE INVENTION

Figure 1:
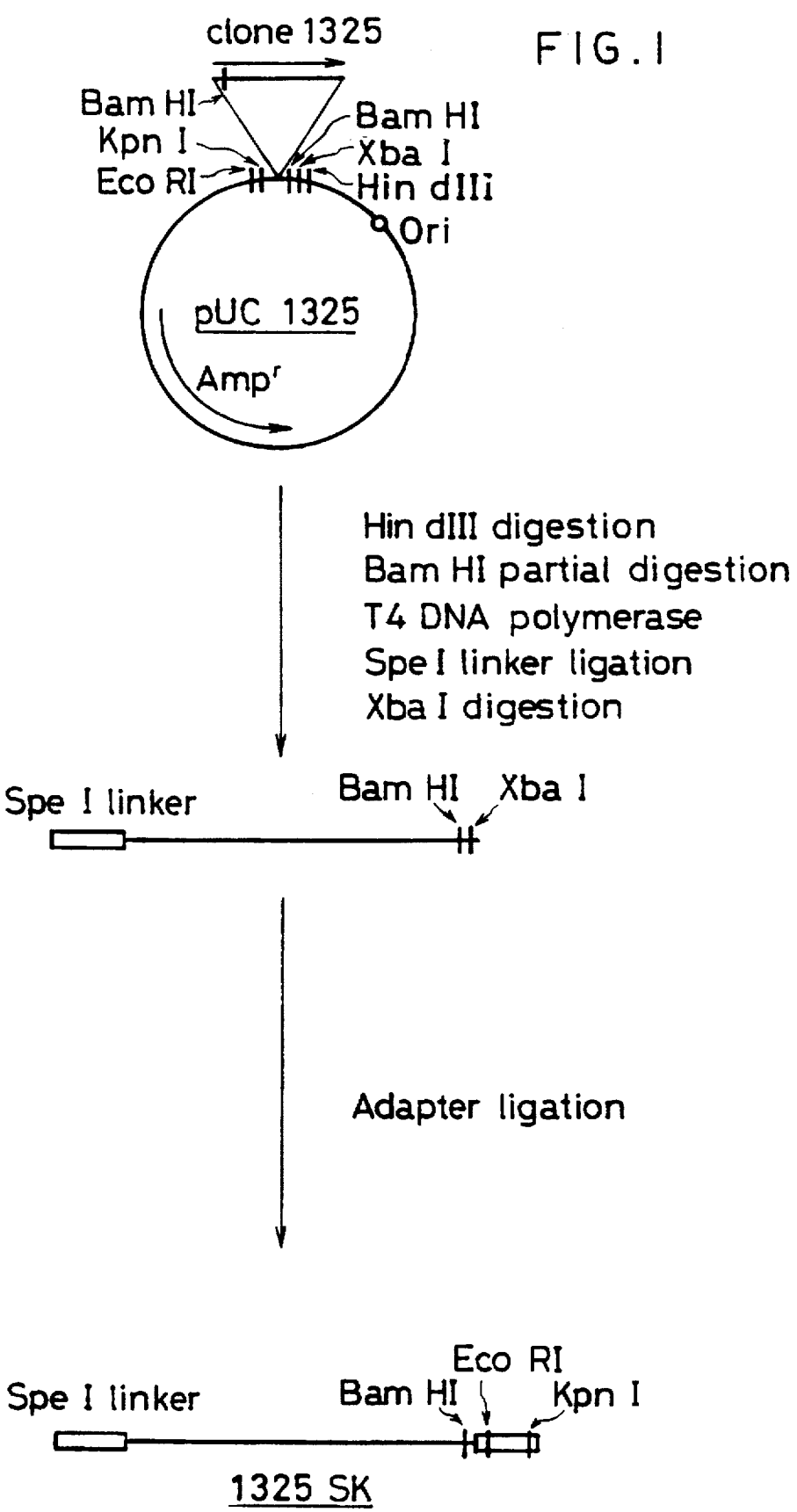
FIG. 1 shows the steps of constructing DNA fragment 1325SK containing the base sequence of clone J1-1325.

E2/NS1 protein of the present invention is a protein derived from the region called the second envelope protein or the first nonstructural protein, which is encoded by the genome of HCV. Examples of the proteins are illustrated in SEQUENCE ID Nos.2, 4, 5, 7, 9, 11, 13, 15, 17, 19, 21 and 22 in SEQUENCE LISTING. Proteins obtained from such proteins by deleting, inserting, modifying or adding a part of amino acids are encompassed in the scope of the present invention provided that they maintain the reactivity with the serum of the patient of hepatitis C. (1) Method of preparing clones of CDNA derived from the serum of the patient of hepatitis C, which are shown in SEQUENCE ID Nos. 1, 3 and the nucleotide sequence encoding SEQ ID NO:3 of SEQUENCE LISTING and determining the base sequence thereof Genes or DNA fragments coding for novel polypeptides, which are shown in SEQUENCE ID Nos. 1, 3 and the nucleotide sequence encoding SEQ ID NO:3 of SEQUENCE LISTING can be prepared, for example, by a method described below.

Since there exists a trace of HCV in the serum and the genome of HCV is expected to be RNA, it was expected that cloning by Okayama-Berg method or Gubler-Hoffman method of the prior art would be attended by difficulties and, therefore, the following method was conducted to ensure the cloning of the gene susceptible to mutation from a trace of the serum.

The nucleic acid is extracted from the serum of the patient of hepatitis C as described in Example 1 later. Generally, it is preferred to use the serum having an OD value of 3.5 or more measured by a test kit of Ortho Inc. However, the present invention is not limited to the use of the serum having such an OD value. The serum is preferably mixed with transfer RNA (tRNA) as a carrier of virus RNA. The carrier is not limited to tRNA. Any polyribonucleoside can be used as carriers. If tRNA is used, there is an advantage that it can be rapidly confirmed by electrophoresis whether there is a required amount of tRNA having an intact length. By this confirmation, it can also be confirmed whether virus RNA degradates after being mixed with tRNA as a carrier of virus RNA. As a technique of cloning cDNA from the nucleic acid, it is preferred to use polymerase chain reaction method developed by Saiki et al. (PCR method, Nature, 324, 126, (1986)). First of all, a reverse transcriptase is reacted using virus RNA as a template. In the reaction, any commercially available random primers or synthesized DNA having a base sequence similar to that of primer AS1 which is shown below may be used as a primer.

```
          5'                          3'

AS1:   GCTATCAGCAGCATCATCCA       SEQUENCE ID No. 23
```

A few bases at the 5' end of these sequences may be changed to other bases. Preferably, a few bases within 10 bases from the 5' end and more preferably, a few bases within 5 bases from the 5' end may be changed to other bases. In addition, 4–5 bases, preferably a few bases may be deleted from the sequences at the 5' end of these sequences. Furthermore, any 8–12 bases, preferably 5–6 bases, more preferably a few bases, may be added to the sequences at the 5' end of these sequences.

PCR method is specifically carried out under the conditions described in Example 1. PCR method is carried out as described in Example 1 using the first complementary DNA (1st cDNA) thus obtained as a template to prepare a desired DNA fragment. The conditions of PCR method are suitably selected depending on the cicumstances. Representative examples of sense primers include the following one:

```
          5'                          3'

S1:   CAGITAITCCGGATCCCICAAG      SEQUENCE ID No. 24
```

"I" appearing in the sequence means inosine. A few bases at the 5' end of these sequences may be changed to other bases. Preferably, a few bases within 10 bases, more preferably, within 5 bases from the 5' end may be changed to other bases. In addition, 4–5 bases, preferably a few bases may be deleted from the sequences at the 5' end of these sequences. Furthermore, any 8–12 bases, preferably 5–6 bases, more preferably a few bases may be added to the sequences at the 5' end of these sequences.

The DNA fragment thus obtained is inserted at one of cloning sites such as Sma I site of a cloning vector such as pUC19 according to conventional technique. Using a plasmid having this DNA fragment, the base sequences of at least 3 clones are determined independently regarding the both strands. The determination of the base sequences can be easily carried out by a dideoxy method using, for example, 7-deaza sequence kit available from Takara Shuzo Co., Ltd. or fluorescence sequencer GENESIS 2000 system available from Du Pont according to the protocol thereof. When the DNA fragment has a site which is considered difficult to determine the base sequence or has more than about 180 base pairs, a subcloning may be carried out according to conventional technique. SEQUENCE ID Nos.1–3 of SEQUENCE LISTING show the amino acid sequences of the proteins assumed from the base sequences of the DNA fragments thus determined.

Clone J1-1325 (SEQUENCE ID No.1), clone N27, clone N19, H19 and Y19 (nucleotide sequence encoding SEQUENCE ID No. 3) were prepared with the serums of different patients. Clone MX24 (nucleotide sequence encoding SEQUENCE ID No.3) was prepared with a pool of the serums of the patients of hepatitis C. The clones shown in SEQUENCE ID Nos.1–3, which were prepared using a combination of primer S1 with primer AS1 correspond to the same region in the gene of HCV.

Antigen proteins derived from E2/NS1 protein regions shown in SEQUENCE ID Nos.2, 4, 5, 7, 9, 11, 13, 15, 17, 19, 21, and 22 of SEQUENCE LISTING can also be used in the present invention.

The antigen protein of SEQUENCE ID No.7 can be obtained by expressing cDNA described in Journal of Virology, 65, 1105–1113, (1991). The antigen protein of SEQUENCE ID No.9 can be obtained by expressing cDNA described in Proceedings of the National Academy of Sciences of the USA, 87, 9524–9528, (1990). The antigen protein of SEQUENCE ID No.11 can be obtained by expressing cDNA described in The fiftieth general meeting of Japanese Cancer Society, 379, (1991). The antigen protein of SEQUENCE ID No.13 can be obtained by expressing cDNA described in European Patent No.0,388,232 (1990). The antigen proteins of SEQUENCE ID Nos.15 and 17 can be obtained by expressing cDNAs described in Proceedings of the National Academy of Sciences of the U.S.A., 88, 3392–3396, (1991). The antigen proteins of SEQUENCE ID Nos.19 and 21 can be obtained by expressing cDNAs described in Japanese Journal of Experimental Medicine, 60, 167–177, (1990). The antigen protein of SEQUENCE ID No.22 can be obtained by expressing cDNA described in Biochemical and Biophysical Research Communications, 175, 220–228, (1991). The sequences shown in SEQUENCE ID Nos.6–22 correspond to the same region as that of the sequences shown in SEQUENCE ID Nos.1–5. (2) Expression of polypeptides encoded by the clones prepared in step (1)

In order to produce E2/NS1 protein, it is necessary to select an appropriate host-vector system which is able to stably express the protein. Further, it is required that the expressed E2/NS1 protein has the same level of biological activity, that is, antigenicity as that of HCV. Considering that natural E2/NS1 protein is expected to be a glycoprotein and that E2/NS1 protein contains many cysteine residues and the positions of the thiol bonds between the cysteine residues and the higher-order structure of the protein are important to maintain the activity, it is desired to express the protein in such an animal cell host as CHO cell, COS cell, mouse L cell, mouse C127 cell and mouse FM3A cell, preferably CHO cell. When these cells are used as hosts, it is expected that processed E2/NS1 protein is produced by introducing E2/NS1 gene having a signal-like sequence of from the 32 position to the 44 position of the amino acid sequences shown in SEQUENCE ID NOs. 2, 4, 5, 7, 9, 11, 13, 15, 17, 19, 21 and 22 into the cell. Expression plasmids for these animal host cells can be constructed as follows:

As promoters in the animal cells, one can use the active-type promoter of adenovirus EIA gene (Biochemical Experiment Lecture, second series, Vol. 1, Techniques for gene investigations II, 189–190 (1986)), the early promoter of SV40, the late promoter of SV40, the promoter of apolipoprotein E gene and SR a promoter (Molecular and Cellular Biology, 8, 466–472, (1988)), preferably the promoter of SV40 and SR α promoter.

A DNA fragment of a gene coding for E2/NS1 protein containing the signal-like sequence is inserted downstream of the promoter in a direction of the transcription. When the expression vector of E2/NS1 protein is constructed, a ligated gene fragment of at least two gene fragments coding for E2/NS1 protein may be inserted downstream of the promoter. At least two units of DNA fragments ligated upstream of the 5' end of the D NA fragment of the gene coding for E2/NS1 protein with such a promoter as that of SV40 may be ligated together in the same direction of the transcription and then inserted in the vector. Polyadenylation sequence is required to be present downstream of the gene coding for E2/NS1 protein. For example, at least one of polyadenylation sequences derived from SV40 gene, β-globin gene or metallothionein gene is required to be present downstream of the gene coding for E2/NS1 protein. When at least two of the DNA fragments containing the gene coding for E21NS1 protein ligated to the promoter are ligated, the polyadenylation sequence may be present at each 3' end of the gene coding for E2/NS1 protein.

In transforming an animal cell such as CHO cell with this expression vector, thereof the selective marker is desired. Examples of the selective markers include DHFR gene expressing methotrexate resistance (Journal of Molecular Biology, 159, 601, (1982)), Neo gene expressing antibiotic G-418 resistance (Journal of Molecular Applied Genetics, 1, 327, (1982)), Ecogpt gene derived from *E. coli*, expressing mycophenol acid resistance (Proceedings of the National Academy of Sciences of the U.S.A., 78, 2072, (1981)), hph gene expressing antibiotic hygromycin resistance (Molecular and Celluar Biology, 5, 410, (1985)) and the like. A promoter such as the aforementioned promoter derived from SV40 and the promoter of TK gene of Herpes virus is inserted upstream of the 5' end of each drug resistance gene. The aforementioned polyadenylation sequence are contained downstream of the 3' end of each drug resistance gene. When such a drug resistance gene is inserted in the expression vector of E21NS1 protein, it may be inserted downstream of the polyadenylated site in the gene coding for E2/NS1 protein in a right direction or a reverse direction. These expression vectors do not require any co-transfection with another plasmid containing a selective marker gene in preparing a transfect.

In the case where such a selective marker gene is not inserted in the expression vector of E2/NS1 protein, a vector having a selective marker of the transfect, such as pSV2neo (Journal of Molecular Applied Genetics, 1, 327, (1982)), pMBG (Nature, 294, 228, (1981)), pSV2gpt (Proceedings of the National Academy of Sciences of the U.S.A., 78, 2072, (1981)), pAd-D26-1 (Journal of Molecular Biology, 159, 601, (1982)) and the like may be used together with the expression vector of E2/NS1 protein to conduct co-transfection. The transfect can be easily selected by gene expression of the selective marker gene.

Examples of methods of introducing the expression vector into the animal cell include calcium phosphate method (Virology, 52, 456, (1973)) and electroporation method (Journal of Membrane Biology, 10, 279, (1972)). Calcium phosphate method is used in general.

The transfected animal cell can be cultured by a float culture or an adherent culture in the conventional manner. The cultivation can be conducted in a medium such as MEM, Ham, F-12 and the like in the presence of 5–10% of serum or a suitable amount of insulin, dexamethasone and transferrin or in the absence of serum. The animal cell expressing E2/NS1 protein can be detected by fluorescent antibody technique using the serum of the patient according to the conventional method. The cloning is carried out by limiting dilution according to the conventional method to establish a cell line stably producing E2/NS1 protein.

E2/NS1 protein derived from HCV gene, thus obtained can be used as HCV antigen which reacts immunologically with the serum containing HCV antibody and therefore, is useful for the confirmation or the detection of the presence of Anti-HCV antibody in samples including blood or serum. Examples of the immunoassays include RIA (radioimmunoassay), ELISA (enzyme-linked immunoadosorbent assay), fluorescent antibody technique, agglutination reaction including latex fixation, immuno precipitation and the like. In the detection, a labelled antibody is usually used. A labelling substance such as a fluorescent substance, a chemoluminescent substance, a radioactive substance, a dyeing substance and the like can be used. Accordingly, using the above E2/NSI protein derived from HCV gene as an antigen, the diagnostic reagent for hepatitis C according to the present invention can be prepared.

The reagent containing the protein having a sugar chain, which is derived from E2/NS1 region according to the present invention makes the confirmation or the detection of the presence of anti-HCV antibody in samples including blood or serum possible. The use of the reagent according to the present invention makes highly sensitive diagnosis of hepatitis C possible.

The present invention will be explained in more detail with reference to the following non-limiting examples.

EXAMPLE 1

(1) Extraction of the nucleic acid from the serum of the patient of hepatitis C

Twenty-five milliliters of a Tris buffer (50 mM Tris-HCl (pH 8.0), 1 mM EDTA and 100 mM NaCl) were added to 10 ml of the serum of the patient of hepatitis C, which showed at least 3.5 of an OD value by a HCV EIA kit available from Ortho Inc. After being mixed, the mixture was centrifuged at 20,000×g at 20° C. for 20 minutes. The obtained supernatant was centrifuged at 100,000×g at 20° C. for additional 5 hours. One point five milliliters of a Protenase K solution (1% sodium dodecyl sulfate, 10 mM EDTA, 10 mM Tris-HCl (pH 7.5), 2 mg/ml Protenase K (available from Pharmacia Co.) and 6.6 μg of a yeast tRNA mixture) were added to the precipitate. After the precipitate was dissolved in the Protenase K solution, the obtained solution was maintained at 45° C. for 90 minutes. The mixture was subjected at least four times to a phenol/chloroform treatment which comprises the steps of adding an equivalent amount of phenol/chloroform, violently agitating and then centrifuging the mixture to collect an aqueous phase containing a nucleic acid. Then, a chloroform treatment was carried out at least 2 times. To the obtained aqueous phase, one-tenth amount of 3M sodium acetate or an equivalent amount of 4M ammonium acetate, and 2.5-fold volume of ethanol were added and the mixture was left to stand at −20° C. overnight or −80° C. for at least 15 minutes. The mixture was centrifuged at 35,000 rpm for 4 hours by a SW41Ti rotor (available from Beckmann Co.) to collect a nucleic acid as a precipitate.

(2) Synthesis of cDNA (2-1) Synthesis of an RNA sample

After the nucleic acid obtained in step (1) was dried, 30 μl of water and 10 μl of ribonuclease inhibitor (100 units/μl, available from Takara Shuzo Co., Ltd.) were added thereto to dissolve the nucleic acid. The following synthesis of CDNA was carried out using the obtained nucleic acid solution.

(2-2) Synthesis of cDNA using an anti-sense primer

To 2 μl of the aqueous solution of the nucleic acid prepared in step (2-1), 1 μl of an anti-sense primer (synthesized DNA primer AS1 ; 15 pmoles/ μl), 2 μl of 10×RT buffer (100 mM Tris-HCl (pH 8.3) and 500 mM of KCl), 4 μl of 25 mM MgCl$_2$, 8 μl of 2.5 mM 4dNTP and 1 μl of water were added and the mixture was maintained at 65° C. for 5 minutes and at room temperature for 5 minutes. Subsequently, 1 μl of 25 units of a reverse transcriptase (available from Life Science Co.) and 1 μl of a ribonuclease inhibitor (100 units/ μl, available from Takara Shuzo Co., Ltd.) were added to the mixture and then the resulting mixture was maintained at 37° C. for 20 minutes, then at 42° C. for 30 minutes and finally at 95° C. for 2 minutes. Immediately thereafter, the mixture was cooled to 0° C. (Synthesis of complementary DNA). The DNA having a specific sequence was amplified using 10 μl of the DNA sample according to Saiki's method (Nature, 324, 126, (1986)), so-called PCR method as follows:

Water was added to a mixture of 10 μl of the above DNA sample, 10 μl of 10×PCR buffer (100 mM of Tris-HCl (pH 8.3), 500 mM of KCl, 15 mM of MgCl$_2$, and 1% of gelatin), 8 μl of 2.5 mM 4dNTP, 2 μl of the synthesized DNA primer used in the synthesis of the complementary DNA (150 pmoles/ μl), 3 μl of a synthesized DNA primer corresponding to the DNA primer (15 pmoles/ μl) (which is complementary to the synthesized DNA primer used in the synthesis of the complementary DNA, i.e., the aforementioned primer S1) to prepare 100 μl of an aqueous solution. After the solution was maintained at 95° C. for 5 minutes, it was cooled rapidly to 0° C. One minute after the cooling, the solution was mixed with 0.5 μl of Taq DNA polymerase (7 units/ μl, Trade Name "AmpliTaqTM" available from Takara Shuzo Co., Ltd.) and then mineral oil was layered on the mixture. This sample was incubated on a DNA Thermal Cycler available from Perkin Elmer Cetus Co. at 95° C. for 1 minute, at 40°–55° C. for 1 minute, and at 72° C. for 1–5 minutes for 25 cycles. After the sample was incubated finally at 72° C. for 7 minutes, the reaction aqueous solution was subjected to a phenol/chloroform treatment and a precipitation treatment with ethanol to obtain amplified DNA fragments.

The above precipitation treatment with ethanol was carried out by mixing the aqueous phase with a one-tenth amount of 3M sodium acetate or an equivalent amount of 4M ammonium acetate together with a 2.5-fold volume of ethanol, centrifuging the mixture at 15,000 rpm at 4° C. for 15 minutes by a rotor having a radius of about 5 cm and drying the precipitate.

(3) Cloning of the amplified DNA fragments and Determination of the base sequences thereof At least 1 pmole of the DNA fragments obtained by the method described in step (2-2) was treated with T4 DNA polymerase (available from TOYOBO CO., LTD) to make blunt ends (Molecular Cloning, 1982, Cold Spring Harbor Laboratory Press). After a phosphoric acid group was introduced into the DNA fragment at the 5' end with polynucleotide kinase (available from TOYOBO CO., LTD) (Molecular Cloning, 1982, Cold Spring Harbor Laboratory Press), the DNA fragment was inserted at Sma I site present in the multicloning sites of pUC19 cloning vector using a ligation kit (available from Takara Shuzo Co., Ltd.).

The vector DNA prepared in the following procedure was used in the ligation in an amount of 5–10 ng. pUC18 cloning vector was cleaved with restriction enzyme Sma I (available from TOYOBO CO., LTD) and then subjected to a phenol/chloroform treatment and a precipitation treatment with ethanol. Subsequently, this was treated with alkaline phosphatase (available from Boehringer Mannheim) to conduct the dephosphorylation at the 5' end (Molecular Cloning, 1982, Cold Spring Harbor Laboratory Press), followed by a phenol/chloroform treatment and a precipitation with ethanol. The competent cell of E. coli JM109 or DH5 (available from TOYOBO CO., LTD) was transformed with the DNA prepared in the above procedure. The procedure of the transformation was according to the protocol of COMPETENT HIGH prepared by TOYOBO CO., LTD. At least 20 transformants transformed with the pUC18 cloning vector having the DNA fragment obtained by the method described in step (2-2) using the combination of the aforementioned primers were prepared.

Plasmid DNA pUC1325 shown in FIG. 1 was prepared from the obtained transformant in the conventional method and the base sequence of the plasmid was determined by a 7-deaza sequence kit available from Takara Shuzo Co., Ltd. or a fluorescence sequencer GENESIS 2000 system available from Du Pont. Two kinds of synthesized primers, 5'd(GTAAAACGACGGCCAGT)3' (SEQUENCE ID No. 25) and 5'd(CAGGAAACAGCTATGAC) 3' (SEQUENCE ID No. 26) were used to determine a base sequence of the +strand and that of the –strand of the DNA fragment. The DNA fragment had the same base sequence as that shown in SEQUENCE ID No. 1 of SEQUENCE LISTING. The amino acid sequence shown in SEQUENCE ID No. 2 of SEQUENCE LISTING is encoded by the +strand of the gene derived from HCV and inserted in the plasmid of the transformant.

The amino acid sequence encoded by the DNA fragment obtained was compared with the reported sequences of hepatitis C viruses. In step (2-2) of Example 1, three clones were obtained from the serum of one patient. The determination of the base sequence of the clones reveals that the patient carries several kinds of viruses.

(4) Preparation of a plasmid expressing E2/NS1 protein

FIGS. 1–6 show a procedure of preparing a plasmid expressing E2/NS1 protein.

(4-1) Preparation of DNA fragment 1325SK

The DNA fragment of clone 1325 contained in plasmid pUC1325 obtained in step (3) was inserted at Sma I site of pUC18 so that the fragment had KpnI site of pUC18 at the 5' end of the +strand of clone 1325 coding for E2/NS1 protein and Bam HI site of pUC18 at the 3' end. After complete digestion with restriction enzyme Hin dIII, the fragment was partially digested with restriction enzyme Bam HI to obtain a DNA fragment which was cleaved not at Bam HI site within the vector but only at another Bam HI site present in clone 1325. The DNA fragment contains from the Bam HI site present at the 5' end to the 3' end of clone 1325 which was the DNA fragment obtained in step (2-2), which was derived from the gene of HCV.

Subsequently, as shown in FIG. 1, the DNA fragment was treated with T4 DNA polymerase to make blunt ends. After being ligated with SpeI linker consisting of the sequence of 5' pGGACTAGTCC 3' (SEQUENCE ID No. 27) (available from New England Biolab Co.), the fragment was cleaved with restriction enzyme Xba I (the Xba I site of the fragment was derived from plasmid pUC18). The following adaptor was ligated to Xba I site at the 3' end to obtain DNA fragment 1325SK.

5' p CTAGAGAATTCGGTAC  3'   (SEQUENCE ID No. 28)
3'        TCTTAAGCp     5'

(4-2) Construction of plasmid pSRNot

Expression vector pAC316 reported in Journal of Virology, 65, 3015–3021, (1991) was cleaved with restriction enzyme Tth 111I at Tth111I site present at the 3' end of 3' poly A region. T4 DNA polymerase was acted on the cleaved vector to make blunt ends. The fragment between SaiII site and Eco RI site of plasmid pmoRE (FIG. 2) reported by Ikeda et al (Gene, 71, 19–27, (1988)) was cut out and T4 DNA polymerase was acted on the fragment to make blunt ends.

Figure 2:
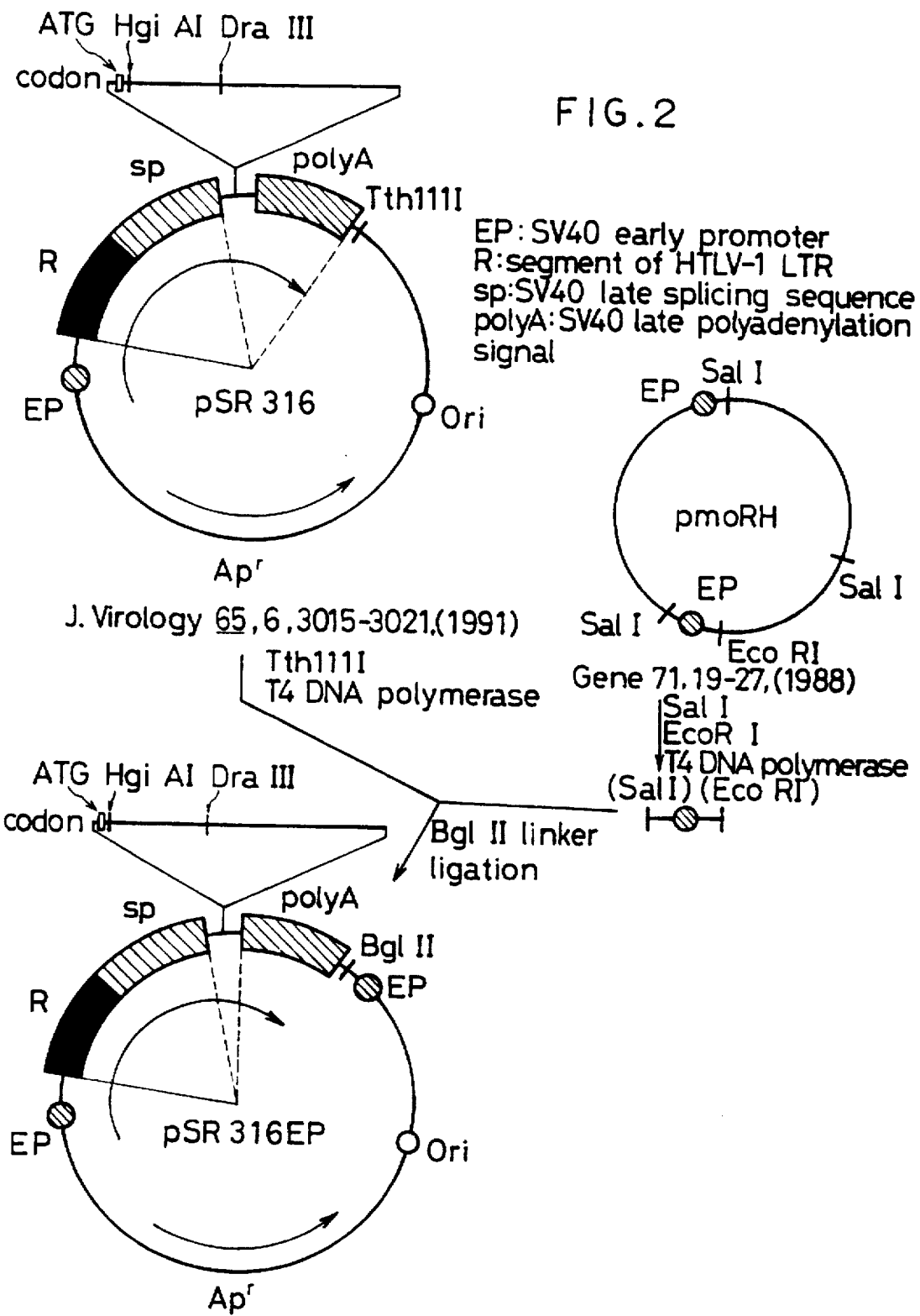
FIG. 2 shows the steps of constructing plasmid pSR316EP.

As shown in FIG. 2, the DNA fragment derived from pAC316 and the DNA fragment derived from pmoRH were ligated together with Bgl II linker (available from Takara Shuzo Co., Ltd.) to obtain plasmid pSR316EP containing one BglII linker and one DNA fragment containing the early promoter of SV40 derived from pmoRH. As shown in FIG. 3, after plasmid pSR316EP was cleaved with restriction enzymes Hgi AI and Dra III. T4 DNA polymerase was acted on the plasmid to make blunt ends. Then, one Not I linker was introduced in the plasmid to obtain plasmid pSRNot (FIG. 3). Namely, NotI linker was prepared by synthesizing DNA having a sequence of 5' AGCGGCCGC 3' and phosphorylating the 5' end by kination (Molecular Cloning second eddition, 11.31–11.44, (1989), Cold Spring Harbor Laboratory Press).

Figure 5:
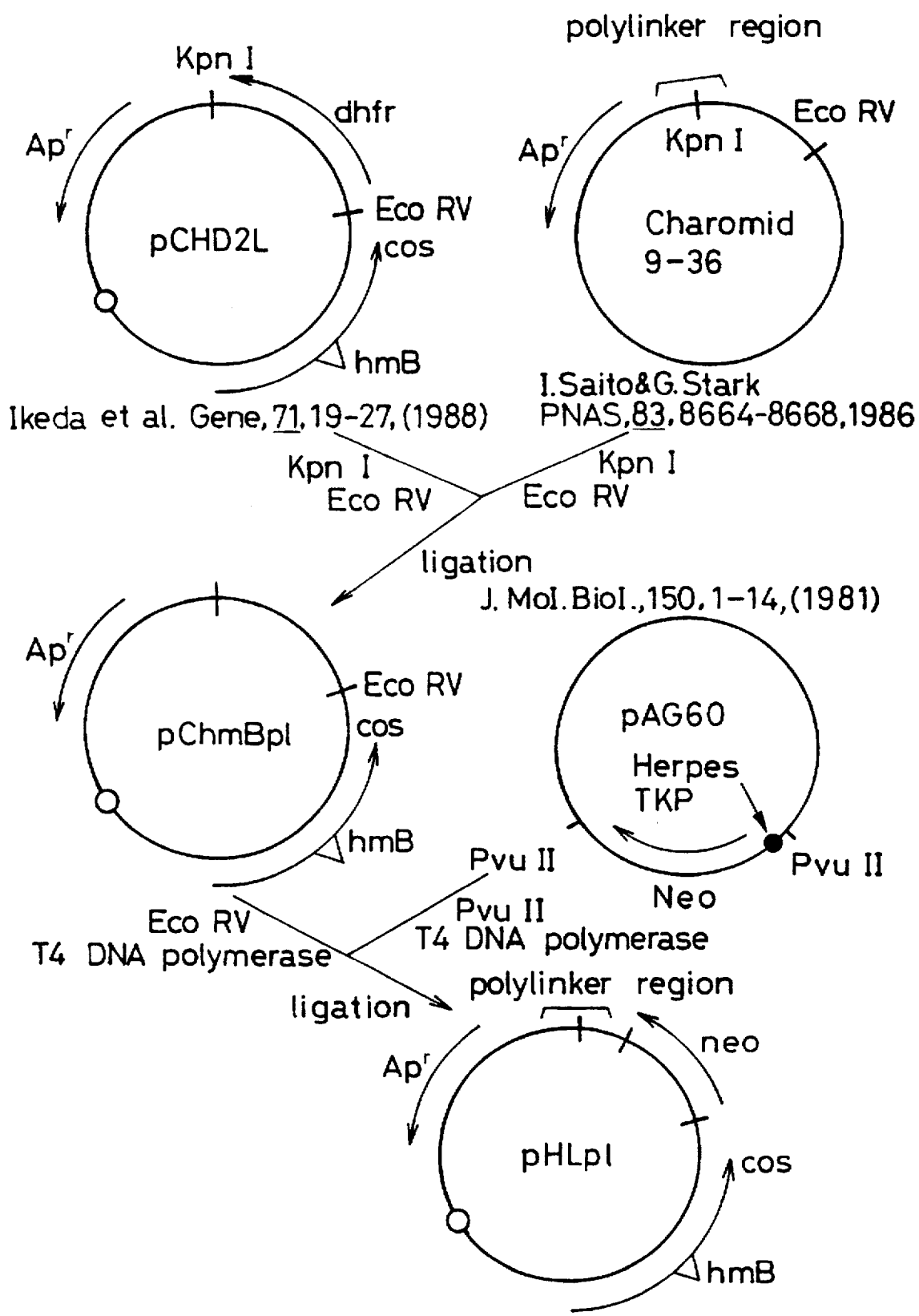
FIG. 5 shows the steps of constructing plasmid pHLp1.

Subsequently, dhfr gene was cut out from plasmid pCHD2L reported by Ikeda et al in Gene, 71, 19–27, (1988) using restriction enzymes Kpn I and Eco RV and Kpn I-EcORV fragment of plasmid Charomid9–36 described in Proceedings of the National Academy of Sciences of the U.S.A., 83, 8664–8668, (1986) was inserted in the deleted dhfr gene region instead of the KpnI- EcoRV fragment coding for dhfr gene as shown in FIG. 5 to obtain plasmid pChmBp1. The plasmid contains a polylinker derived from plasmid Charomid9-36.

Then, plasmid pAG60 reported by Garapin et al. in journal of Molecular Biology, 150 , 1–14, (1981) was cleaved with restriction enzyme Pvu II to obtain a Pvu II fragment coding for a neomycin gene. After plasmid pChmBp1 was cleaved with restriction enzyme Eco RV and then T4 DNA polymerase was acted to make blunt ends, the fragment obtained was ligated to the Pvu II fragment to obtain plasmid pHLp1 which contained the neomycin gene derived from plasmid pAG60 at the Eco RV site of plasmid pChmBp1 (FIG. 5).

(4-3) Construction of expression vector paSR1325X-3

As shown in FIG. 4, after plasmid pSRNot obtained in step (4-2) was cleaved with restriction enzyme Not I and then with T4 DNA polymerase to make blunt ends, this was cleaved with restriction enzyme Kpn I. The obtained DNA fragment was ligated to DNA fragment 1325SK obtained in step (4-1) to obtain expression vector paSR1325X-3 having only one DNA fragment 1325SK (FIG. 4).

(4-4) Construction of expression vector pHL16SR1325

Figure 6:
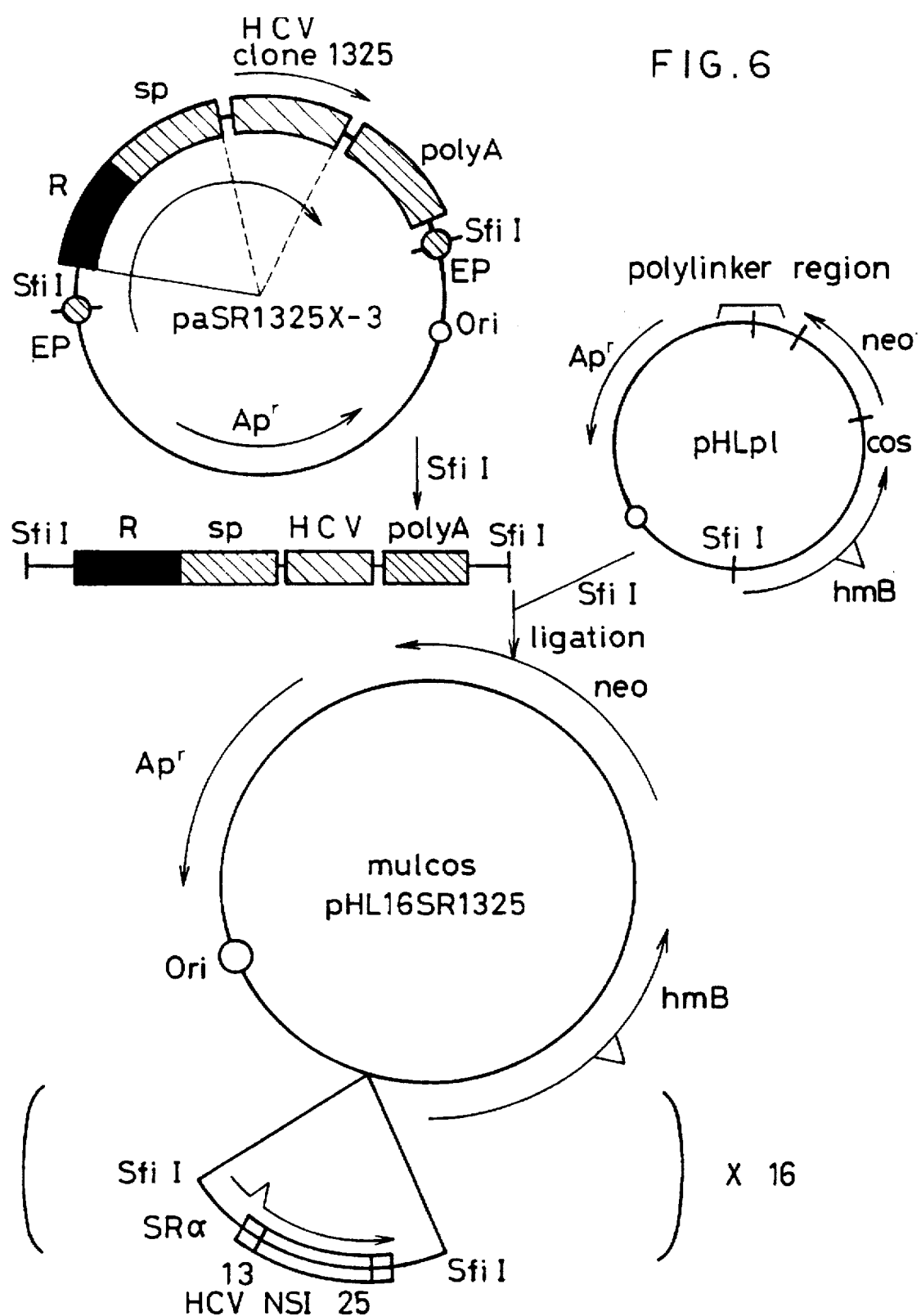
FIG. 6 shows the steps of constructing expression vector mulcos pHL16SR1325 having 16 DNA fragments coding for E2/NS1 protein.

As shown in FIG. 6, expression vector paSR1325X-3 obtained in step (4-3) was cleaved with restriction enzyme Sfi I to prepare two fragments one of which was an expression unit of clone 1325. The Sfi I sites were present in an initial promoter of SV40. Five µg of the Sfi I fragment having the expression unit of clone 1325 was ligated to 50 ng of the fragment obtained by cleaving expression vector pHLp1 with restriction enzyme Sfi I in 10 µl of a reaction solution using a ligation kit available from Takara Shuzo Co., Ltd. according to a protocol for the ligation kit to obtain expression vector pHL16SR1325 (FIG. 6).

The vector had successive sixteen DNA fragments 1325SK having at the Sfi I site of expression vector paSR1325X-3 the expression unit of clone 1325 which was a gene coding for E2/NS1 protein. In the vector, all of the DNA fragments 1325SK were inserted downstream of SV40 promoter of expression vector paSR1325X-3 in a direction of transcription.

(5) obtaining a cell line constantly expressing E2/NS1 protein Expression vector pHL16SR1325 prepared in step (4) was recovered from the recombinant *E. coli* DH1 strain, purified according to the conventional technique described in Molecular Cloning second edition, 1989, Cold Spring Harbor Laboratory Press to obtain a large amount of the expression plasmid DNA. CHO cells were transfected with the plasmid DNA according to the method described in Ausubel et al. (Current Protocols in Molecular Biology, Greene Publishing Associates and Wiley-Interscience, Capter 9.1.1–9.1.4, (1987)) as follows:

CHO cells were cultured in Ham F-12 medium containing 10% of fetal calf serum (FCS) in a plate having a diamer of 6 cm until the cells were in semiconfluent condition. Then, the medium was removed from the plate and a DNA solution was dropwise added thereto. The DNA solution was previously prepared by the following procedure.

Three hundred µl of 2×HEBS solution (2×HEBS solution; 1.6% sodium chloride, 0.074% potassium chloride, 0.05% $Na_2HPO_4.12H_2O$, 0.2% dextrose and 1% HEPES (pH 7.05)) were mixed with 10 µg of the plasmid DNA in each plate and sterilized water was added to the mixture to prepare a solution of 570 µl. The solution was charged in an Eppendorf centrifuge tube. The DNA solution was violently agitated by a Vortex mixer for 1–2 seconds while adding 30 µl of 2.5M calcium chloride solution thereto. The DNA solution was agitated by a Vortex mixer at about 10-minute intervals during being left to stand for 30 minutes. The obtained DNA solution was added to the aforementioned CHO cells and the CHO cells were left to stand at room temperature for 30 minutes. Then, 5 ml of Ham F-12 medium containing 10% of FCS available from GIBCO·Co. were added to the plate and the culture was incubated at 37° C. under air containing 5% carbon dioxide for 4–5 hours. Subsequently, the medium was removed from the plate and the cells were washed with 5 ml of a 1×TBS ++ solution (1×TBS ++ solution; 25 mM Tris-HCl (pH 7.5), 140 mM sodium chloride, 5mM potassium chloride, 0.6 mM disodium hydrogen phosphate, 0.08 mM calcium chloride and 0.08 mM magnesium chloride). After the 1×TBS ++ solution was removed, 5 ml of a 1×TBS ++ solution containing 20% of glycerol was added to the cells and the culture was left to stand at room temperature for 1–2 minutes. After the supernatant was removed from the plate, the cells were washed again with 5 ml of a 1×TBS ++ solution and cultured in 5 ml of fresh Ham F-12 medium containing 10% of FCS in the plate at 37° C. under air containing 5% carbon dioxide for 48 hours. Then, the medium was removed and the cells were washed with 5 ml of a 1×TBS ++ solution. The cells were treated with a trypsin-EDTA solution (available from Sigma Co.) and left to stand at room temperature for 30 seconds. Five minutes after the trypsin-EDTA solution was removed, the cells attached to the wall of the plate were peeled adding 5 ml of Ham F-12 medium containing 10% of FCS. The cells cultured in one plate having a diameter of 5 cm were divided in ten plates having a diameter of 9 cm and cultured in the plates containing drug G418 (G418 sulfate (GENETICIN) available from GIBCO Co.) in a concentration of 600 µg/ml.

Ten days after the cultivation, grown cells having G418 resistance were isolated and cultured for about 7 days in 1 ml of Ham F-12 medium containing 10% of FCS in a 24 well titer plate each well of which has an area of about 3.1 $cm^2$.

A part of the cells were cultured on slide glass (Lab-Tek Chamber Slides, Nunc4808 available from Japan Inter Med Co.) overnight. After being rinsed with phosphate buffered saline (PBS), the slide glass was immersed in cold acetone-methanol (1:1) solution and maintained at −20° C. for 15 minutes to fix the cells. The cells fixed on the slide glass were reacted with the serum of the patient of hepatitis C 20-fold diluted with PBS at 37° C. for 30 minutes. Then, the slide glass was washed three times with PBS for 5 minutes and reacted with FITC-labelled rabbit anti-human IgG (available from Daco Japan Co.) 50-fold diluted with PBS at 37° C. for 30 minutes. The slide glass was washed three times with PBS for 5 minutes and dried by putting the slide glass between two pieces of filter paper. After the slide glass was sealed with glycerin, the cells on the slide glass were observed under a fluorescence microscope. Screening positive cells as described above, successive three times of limiting dilution were carried out to establish cell line 13L20 constantly producing E2/NS1 protein.

(6) Study of the reactivity of 13L20 cells with the serum of the patient of hepatitis C After 13L20 cells established in step (5) were cultured on Lab-Tek Chamber Slides (Lab-Tek Chamber Slides, Nunc4808 available from Japan Inter Med Co.) overnight and then fixed with a cold acetone-methanol solution, the fixed cells were reacted with 59 serum samples of the patients of hepatitis C. Then, the cells were washed as described above and reacted with the secondary antibody. The observation under a fluorescence microscope revealed that 53 samples were positive. Among the 59 serum samples, 6 samples were judged to be positive using CHO cells constantly producing the first envelope region of HCV.

EXAMPLE 2

Using as a template the DNA fragment described in Example 11 (3) of the specification of European Patent Application No. 92109812.5 filed on Jun. 11, 1992 (TITLE OF THE INVENTION "Gene or DNA fragments derived from hepatitis C virus, polypeptides encoded thereby, and method of producing thereof"), PCR reaction was carried out in the same manner as that of Example 1 using the same primer to obtain a DNA fragment corresponding the same region as that of clone J1-1325 shown in SEQUENCE ID No. 1 of SEQUENCE LISTING. The region was a DNA fragment encoding for E2/NS1 protein like clone J1-1325. For example, using as a template the DNA fragment clone N27MX24A-1 having a base sequence shown in SEQUENCE ID No.31 of SEQUENCE LISTING described in the specification of the aforementioned European Patent Application filed on Jun. 11, 1992, plasmid pUCN27MX24A-2 was obtained. The base sequence of the DNA fragment coding for E2/NS1 protein, which was cloned in the plasmid is shown in SEQUENCE ID No. 3 of SEQUENCE LISTING. In addition, MK2724A2 cell line constantly producing E2/NS1 protein was establised by the same procedure as that described in steps (4) and (5) of Example 1. The reactivity of the same samples as Example 1 with the cell line was estimated by the same method as that described in step (6) of Example 1. Results similar to those obtained in step (6) of Example 1 were obtained.

---

What is claimed is:

1. A diagnostic reagent for hepatitis C, which detects anti-second envelope protein/first non-structural protein, E2/NS1, antibodies in a sample, said reagent consisting essentially of a protein represented by an amino acid sequence selected from SEQ ID NOS:2, 4, 5, 7, 9, 11, 13, 15, 17, 19, 21, and 22, said protein being produced by a mammalian cell, wherein said protein comprises a sugar chain.

2. The diagnostic reagent for hepatitis C according to claim 1 wherein the protein is encoded by a base sequence selected from SEQ ID NOS: 1, 3, 6, 8, 10, 12, 14, 16, 18 and 20.

3. The diagnostic reagent for hepatitis C according to claim 1, wherein the protein is produced by a CHO cell.

4. A diagnostic reagent for hepatitis C, which detects anti-E2/NS1 antibodies in a sample, comprising a mammalian cell transformed with a DNA sequence, wherein said DNA sequence comprises a hepatitis C sequence consisting of SEQ ID NOS: 1, 3, 6, 8, 10, 12, 14, 16, 18 or 20, wherein said cell expresses a hepatitis C virus (HCV) protein, and said HCV protein comprises a sugar chain.

5. The diagnostic reagent for hepatitis C according to claim 4 wherein the HCV protein is represented by an amino acid sequence selected from SEQ ID NOS:2, 4, 5, 7, 9, 11, 13, 15, 17, 19, 21, and 22.

6. The diagnostic reagent for hepatitis C according to claim 4, wherein the HCV protein is produced by a CHO cell.

* * * * *